United States Patent
Oikawa et al.

(10) Patent No.: US 7,359,479 B2
(45) Date of Patent: Apr. 15, 2008

(54) RADIOGRAPHIC APPARATUS

(75) Inventors: Shiro Oikawa, Kyoto (JP); Hisanori Morita, Kyoto (JP)

(73) Assignee: Shimadzu Corproation, Kyoto (JP)

( * ) Notice: Subject to any disclaimer, the term of this patent is extended or adjusted under 35 U.S.C. 154(b) by 0 days.

(21) Appl. No.: 11/447,153

(22) Filed: Jun. 6, 2006

(65) Prior Publication Data
US 2006/0274880 A1 Dec. 7, 2006

(30) Foreign Application Priority Data
Jun. 7, 2005 (JP) .............................. 2005-167092

(51) Int. Cl.
*A61B 6/00* (2006.01)
(52) U.S. Cl. .......................... 378/19; 378/15; 378/21; 378/197
(58) Field of Classification Search .............. 378/4–27, 378/193–197, 901; 250/370.08, 370.09
See application file for complete search history.

(56) References Cited

U.S. PATENT DOCUMENTS

2004/0066880 A1 * 4/2004 Oikawa ...................... 378/4

FOREIGN PATENT DOCUMENTS

JP 2004-141656 5/2004

\* cited by examiner

*Primary Examiner*—Courtney Thomas
(74) *Attorney, Agent, or Firm*—Cheng Law Group PLLC

(57) ABSTRACT

An FPD has a detecting plane with detecting elements arranged in rows (u-axis) and columns (v-axis) extending in two intersecting axial directions. In time of primary scanning, the FPD is moved about a sectional axis to maintain the u-axis parallel to a body axis constantly. Consequently, in a reconstruction process, a set of projection points on the detecting plane of X rays having passed through lattice points in one row along the body axis A of an imaginary three-dimensional lattice, is parallel to the u-axis. It is therefore possible to derive all projection data that should be projected back to the lattice points in one row, only from detection signals acquired from the detecting elements in two lines having the set of projection points in between. Thus, the quantity of detection signals required for obtaining the projection data is reduced to perform the reconstruction process at high speed.

20 Claims, 20 Drawing Sheets

Fig.9 F space filter method

RADIOGRAPHIC APPARATUS

BACKGROUND OF THE INVENTION (1) Field of the Invention

This invention relates to radiographic apparatus for use in the medical field, and in industrial fields for performing a non-destructive testing, RI (Radio Isotope) inspection or optical inspection.

(2) Description of the Related Art

A conventional apparatus of this type includes an X-ray tube and a flat panel X-ray detector (hereinafter called "FPD" as appropriate) opposed to each other, and performs a primary scanning by rotating the X-ray tube and X-ray detector together about a sectional axis (also called a primary scanning axis) passing through a site of interest of an object under examination, and a secondary scanning by rotating the X-ray tube and X-ray detector together about an axis (also called a secondary scanning axis, and hereinafter referred to as "body axis") extending substantially perpendicular to the sectional axis. The apparatus acquires a three-dimensional sectional image based on a group of projection data obtained from the FPD at varied points of time during the primary scanning and secondary scanning (as disclosed in Japanese Unexamined Patent Publication No. 2004-141656, for example).

However, the conventional apparatus of such a construction has the following drawback.

When performing a reconstruction process, a three-dimensional lattice is virtually set to the site of interest of the object under examination. This three-dimensional lattice has one side thereof extending parallel to the body axis of the object. Information is given to each lattice point of the three-dimensional lattice based on projection data at a point where an X ray passing through that lattice point falls on the detecting plane of the FPD (hereinafter called simply "projection point of the lattice point"). This process is called back projection. The FPD has detecting elements arranged in matrix form on the detecting plane, and a detection signal is acquired from each detecting element. Projection data at the projection point of each lattice point is derived from detection signals acquired from a plurality of (e.g. four) detecting elements around the projection point.

Consider lattice points arranged in one row extending parallel to the body axis. The projection points of these lattice points are distributed on one straight line. Since the FPD rotates about the sectional axis, this straight line rotates 360 degrees on the detecting plane of the FPD in one primary scan. Therefore, the projection points hardly become parallel to a direction of a row or column of the detecting elements, but are distributed among three or more rows or three or more columns of the detecting elements.

The projection points of lattice points arranged in directions not parallel to the body axis also are distributed among three or more rows or three or more columns of the detecting elements.

In time of calculation, on the other hand, access is made beforehand to a relatively low-speed main memory that stores detection signals, and required detection signals are taken into a relatively high-speed cache memory by designating a start address and range of the detection signals. However, signals from a large number of rows will exceed the capacity of the cache memory. In this case, it is necessary to access the main memory again. It can be advantageous from the viewpoint of effectively using the capacity of the cache memory to divide detection signals into blocks and to take in only required detection signals. However, the main memory must be accessed the number of times corresponding to the number of blocks. Since access to the main memory requires a relatively long time, the greater accessing frequency results in the longer time required for a reconstruction process.

SUMMARY OF THE INVENTION

This invention has been made having regard to the state of the art noted above, and its object is to provide a radiographic apparatus for performing a reconstruction process at high speed.

The above object is fulfilled, according to this invention, by a radiographic apparatus for obtaining three-dimensional sectional images, comprising a radiation source for emitting electromagnetic waves to an object under examination; a detecting device opposed to the radiation source across the object for obtaining projection data of the object from the electromagnetic waves transmitted through the object; a primary scanning device for performing a primary scanning by moving at least the radiation source to rotate a radiation axis linking the radiation source and the detecting device about a sectional axis passing through a site of interest of the object, while inclining the radiation axis at a predetermined angle to the sectional axis; and an image processing device for performing a reconstruction process based on a group of projection data obtained from the detecting device at each point of time in the primary scanning to acquire a three-dimensional sectional image; wherein the detecting device has a flat or curved detecting plane with a plurality of detecting elements arranged in rows and columns extending in two intersecting axial directions for detecting the electromagnetic waves, the rows or columns of the detecting elements being, in time of the primary scanning, constantly parallel to one axis extending perpendicular to the sectional axis and passing through the site of interest of the object.

According to this invention, in time of primary scanning, the rows or columns of the detecting elements arranged on the detecting plane of the detecting device are parallel to one axis extending perpendicular to the sectional axis and passing through the site of interest of the object under examination. The points (projection points) on the detecting plane struck by the electromagnetic waves having passed through imaginary lattice points in one row along the one axis, are arranged parallel to the rows or columns of the detecting elements. It is therefore possible to derive projection data that should be projected back to the lattice points in one row, only from detection signals acquired from the detecting elements in two lines having the projection points of the lattice points in between. The detection signals are projection data for the positions of the detecting elements, and are derived from actual detections. Thus, the quantity of detection signals required for obtaining the projection data is reduced, thereby to perform the reconstruction process at high speed.

In the invention described above, it is preferred that the primary scanning device is arranged to move the radiation source about the sectional axis, and move the detecting device about the sectional axis. Then, the primary scanning can be carried out advantageously.

Preferably, the primary scanning device is arranged also to incline the detecting device according to a position of the detecting device, so that the detecting plane is perpendicular to a direction corresponding the radiation axis from which a component along the one axis is subtracted. Seen from the direction of the one axis extending perpendicular to the sectional axis and passing through the site of interest of the object under examination, the detecting plane appears perpendicular to the radiation axis. In time of the primary scanning, therefore, the detecting device is inclined, within a permissible range, relative to the direction of incidence of the electromagnetic waves while constantly maintaining the rows or columns of the detecting elements parallel to the one axis. This allows a braid or the like to be formed integrally with the detecting plane.

Preferably, the primary scanning device is arranged to move the detecting device along a curve linking intersections of a virtual cylinder about the sectional axis and a virtual cylinder about the one axis. By the virtual cylinder about the sectional axis, the detecting device is opposed to the radiation source moving about the sectional axis. By the virtual cylinder about the one axis extending perpendicular to the sectional axis and passing through the site of interest of the object, the detecting device is reliably inclined within the permissible range while constantly maintaining the rows or columns of the detecting elements parallel to the one axis.

It is also preferred that the primary scanning device is arranged to move the radiation source along the curve linking intersections of the virtual cylinder about the sectional axis and the virtual cylinder about the one axis. Then, the radiation source and detecting device are moved while maintaining the positional relationship between the radiation source and detecting device.

In the above invention, it is preferred that movement of the detecting device by the primary scanning device is realized in a combination of a linear motion component along the one axis and a rotational motion component on an arc about the one axis. The detecting device moves parallel to the one axis extending perpendicular to the sectional axis and passing through the site of interest of the object. In time of the primary scanning, therefore, the rows or columns of the detecting elements are constantly maintained parallel to the one axis. The rotational motion component on the arc about the one axis can reliably incline the detecting device within the permissible range.

It is also preferred that movement of the radiation source by the primary scanning device is realized in the combination of the linear motion component along the one axis and the rotational motion component on the arc about the one axis. Then, the radiation source and detecting device are moved while maintaining the positional relationship between the radiation source and detecting device.

In the above invention, it is preferred that the primary scanning device is arranged to move the detecting device along a curve linking intersections of a virtual cone formed at the predetermined angle about the sectional axis, with an intersection of the one axis and the sectional axis providing an apex, and a virtual cylinder about the one axis. By the virtual cone, the detecting device is opposed to the radiation source. By the virtual cylinder about the one axis extending perpendicular to the sectional axis and passing through the site of interest of the object, the detecting device is reliably inclined within the permissible range while constantly maintaining the rows or columns of the detecting elements parallel to the one axis.

In the above invention, it is preferred that the detecting plane has a braid disposed thereon for removing scattered parts of the electromagnetic waves, the primary scanning device moving the braid with the detecting device. This construction can effectively remove scattered parts of the electromagnetic waves.

In the above invention, the primary scanning device may be arranged to rotate only the radiation source about the sectional axis, and the detecting device is sized to cover varied positions of the radiation source rotated by the primary scanning device, the detecting device standing still when the primary scanning device rotates the radiation source. The detecting device having a sufficiently large detecting plane stands still in time of the primary scanning. Consequently, the rows or columns of the detecting elements are constantly and easily maintained parallel to the one axis extending perpendicular to the sectional axis and passing through the site of interest of the object.

Preferably, the apparatus further comprises a braid disposed on the detecting plane for removing scattered parts of the electromagnetic waves, and a braid moving device for moving the braid in a combination of a linear motion component along the one axis and a rotational motion component on an arc about the one axis, the braid moving device maintaining the braid opposed to the radiation source. The braid can be inclined reliably within a permissible range while constantly maintaining the braid parallel to the one axis extending perpendicular to the sectional axis and passing through the site of interest of the object.

It is also preferred that the apparatus further comprises a secondary scanning device for performing a secondary scanning by moving the radiation source and the detecting device to rotate the radiation axis about the one axis, the image processing device further performing a reconstruction process based on a group of projection data obtained from the detecting device at each point of time in the secondary scanning. By moving the radiation source and detecting device for the secondary scanning, sectional images with isotropic spatial resolution can be obtained of the object under examination.

BRIEF DESCRIPTION OF THE DRAWINGS

For the purpose of illustrating the invention, there are shown in the drawings several forms which are presently preferred, it being understood, however, that the invention is not limited to the precise arrangement and instrumentalities shown.

DESCRIPTION OF THE PREFERRED EMBODIMENTS

Preferred embodiments of this invention will be described in detail hereinafter with reference to the drawings.

First Embodiment

Figure 1:
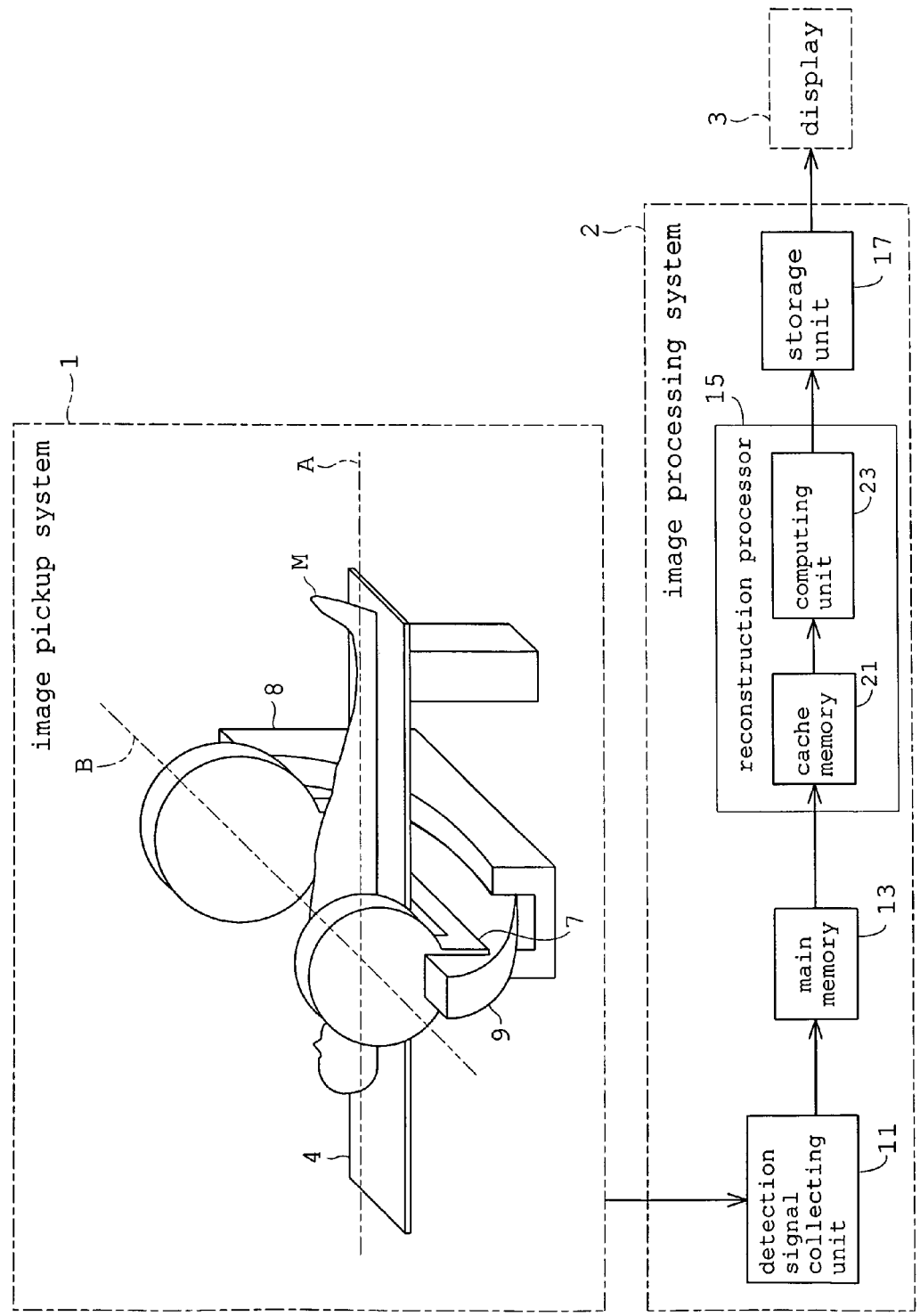
FIG. 1 is a block diagram showing an outline of a radiographic apparatus in a first embodiment.
Figure 2:
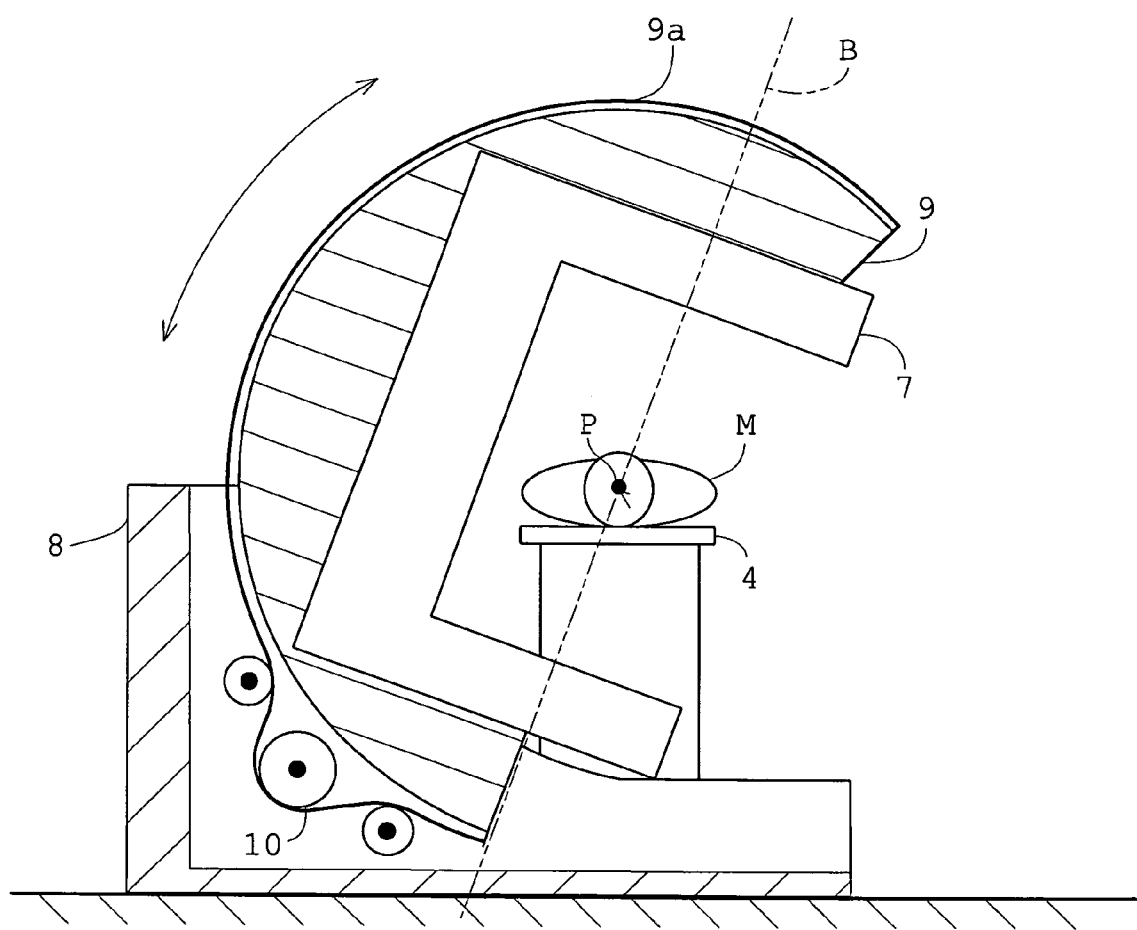
FIG. 2 is a schematic view in vertical section of the radiographic apparatus.
Figure 3:
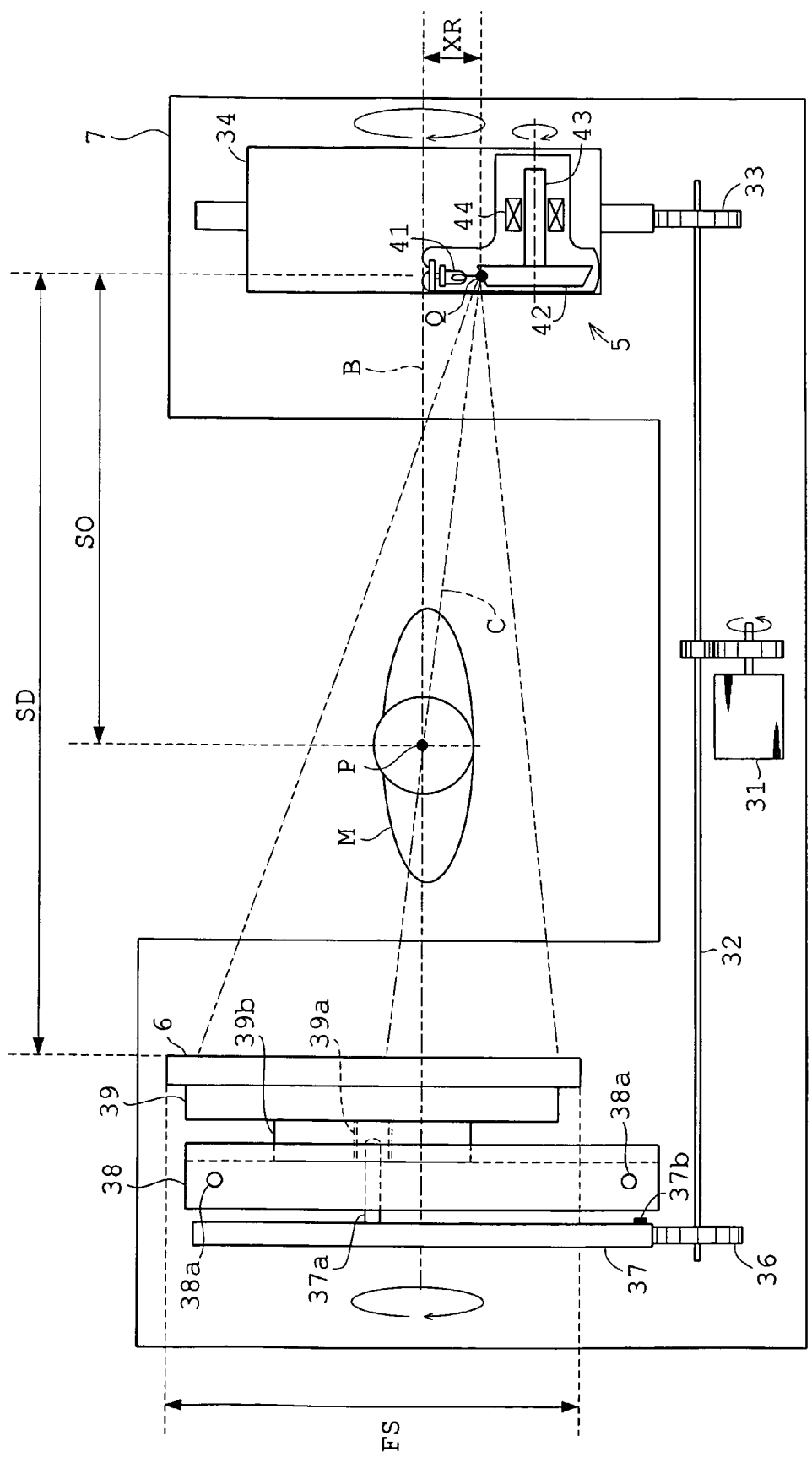
FIG. 3 is a sectional side view of a scan frame.
Figure 4:
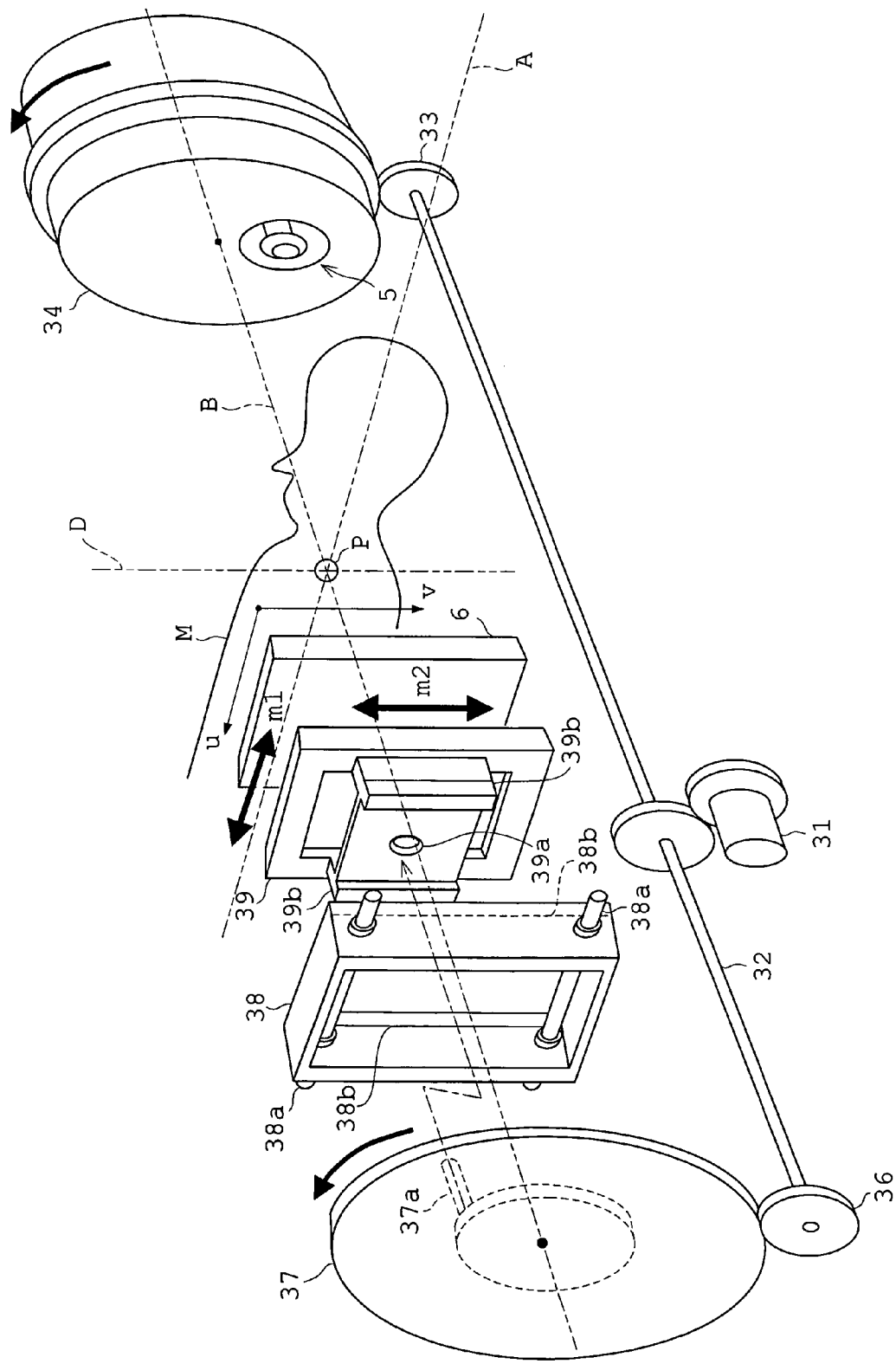
FIG. 4 is a perspective view of an interior of the scan frame.

FIG. 1 is a perspective view showing an outline of a radiographic apparatus in a first embodiment. FIG. 2 is a sectional view on a sectional axis of the radiographic apparatus. FIG. 3 is a sectional view on the sectional axis of a scan frame. FIG. 4 is a perspective view of an interior of the scan frame.

The radiographic apparatus, broadly, is divided into an image pickup system 1 for obtaining projection data of a patient M, an image processing system 2 for processing the projection data and creating a three-dimensional sectional image, and a display 3 for displaying the sectional image created.

The image pickup system 1 includes a top board 4 for supporting the patient M, a scan frame 7 housing a rotating anode X-ray tube 5 and a flat panel X-ray detector (hereinafter abbreviated as "FPD") 6, and a base 8 for supporting the scan frame 7. The base 8 is fixed to a floor surface.

A sectional axis B is an axis that passes through a site of interest P of the patient M, and is a center axis of primary scanning described hereinafter. A body axis A is one of axes extending perpendicular to the sectional axis B and passing through the site of interest P of the patient M, and is a center axis of secondary scanning described hereinafter. The body axis A corresponds to the one axis ("one axis extending perpendicular to the sectional axis and passing through the site of interest of the object under examination") in this invention.

The image processing system 2 includes a detection signal collecting unit 11, a man memory 13, a reconstruction processor 15 and a storage unit 17. The reconstruction processor 15 has a cache memory 21 and a computing unit 23.

Each component will be described hereinafter.

As shown in FIG. 2, a frame holder 9 of approximately semicircle shape is disposed at the back of the scan frame 7 for holding the scan frame 7. The frame holder 9 has a secondary scanning belt 9a attached peripherally thereof. The base 8 has a curved groove formed centrally thereof. A roller 10 is disposed in the groove to be rotatable by a drive mechanism not shown. The frame holder 9 is slidably supported on an inner peripheral surface of the groove, with the secondary scanning belt 9a wound on the roller 10. The frame holder 9, base 8 and roller 10 constitute the secondary scanning device in this invention.

As shown in FIGS. 3 and 4, the scan frame 7 houses, besides the rotating anode X-ray tube 5 and FPD 6, a rotary motor 31, a rotary shaft 32, an X-ray tube gear 33, an X-ray tube case 34, an FPD gear 36, a turntable 37, a holding frame 38 and an FPD support member 39. The X-ray tube gear 33 and FPD gear 36, preferably, are equal in diameter.

The rotary motor 31 is connected to the rotary shaft 32 through gears. The rotary shaft 32 is connected to the X-ray tube case 34 through the X-ray tube gear 33. The X-ray tube case 34 is rotatable about the sectional axis B. The rotary shaft 32 is connected to the turntable 37 through the FPD gear 36. The turntable 37 is rotatable about the sectional axis B.

The rotating anode X-ray tube 5 is mounted in the X-ray tube case 34 as offset from the sectional axis B located at the center of the case 34.

The rotating anode X-ray tube 5 is the rotating anode X-ray tube type as its name suggests. That is, the X-ray tube 5 includes a cathode (filament) 41 for releasing thermions, an anode (target) 42 for generating X rays by accelerated collision with the thermions from the cathode 41, a high-speed rotary shaft 43 for rotating the anode 42 at high speed about its center, and a bearing 44 for rotatably supporting the high-speed rotary shaft 43. The high-speed rotary shaft 43 extends parallel to the sectional axis B. The rotating anode X-ray tube 5 corresponds to the radiation source in this invention.

The rotating anode X-ray tube 5 emits X rays in what is called "cone beam" shape with a predetermined angle of divergence. A center track, or a track extending from a radiation source position (also called the focal position of the X-ray tube) Q of the rotating anode X-ray tube 5 to the FPD 6, is called radiation axis C. The X-ray tube 5 is positioned so that the radiation axis C pass through the site of interest P of the patient M.

The turntable 37 has a holding rod 37a in a position offset from its center. The holding frame 38 has four sides, and the holding rod 37a extends through an opening formed in the holding frame 38. This holding frame 38 has two frame holding rods 38a extending through two opposite sides, and parallel to the body axis A. These frame holding rods 38a are fixed to the scan frame 7. The holding frame 38 has bearings in respective positions thereof penetrated by the frame holding rods 38a, to be slidable only in directions along the body axis A.

The FPD support member 39 has a bearing 39a defining a bore with a rotatable inner peripheral surface. The FPD support member 39 is held by the turntable 37, with the bearing 39a joined with the holding rod 37a. The FPD support member 39 has a back plate 39 attached to the back thereof for contacting the inside of the holding frame 38, so that the FPD support member 39 constantly face a fixed direction. Further, the FPD support member 39 supports the FPD 6 at the front thereof. The FPD support member 39 supports the FPD 6 to be opposed to the rotating anode X-ray tube 5 across the patient M.

The turntable 37 has a counterbalance 37b. The counterbalance 37b is disposed in a position opposed to the holding rod 37a across the center of rotation (sectional axis B) of the turntable 37 and, preferably, adjacent an edge of the turntable 37. The counterbalance 37b is set to balance a moment acting on the holding rod 37a in time of rotation of the turntable 37.

The rotary motor 31, rotary shaft 32, X-ray tube gear 33, X-ray tube case 34, FPD gear 36, turntable 37, holding frame 38 and FPD support member 39 constitute the primary scanning device in this invention. The holding frame 38 corresponds to the restricting device in this invention. The FPD support member 39 corresponds to the support member in this invention.

The FPD 6 has a flat detecting plane. In this embodiment, the detecting plane is square in plan view.

The length FS of one side of the FPD 6, preferably, is derived from the following equation (1):

$$FS=2XR*SD/SO \quad (1)$$

where XR is a turning radius of the radiation source position Q of the rotating anode X-ray tube 5, SO is a distance from the rotation center of the X-ray tube 5 to the site of interest P of the patient M, and SD is a distance from the rotation center of the X-ray tube 5 to the detecting plane of the FPD 6.

The length FS of one side of the FPD 6 is not limited to the above. For example, the length of one side may exceed the value derived from equation (1) above.

Figure 5:
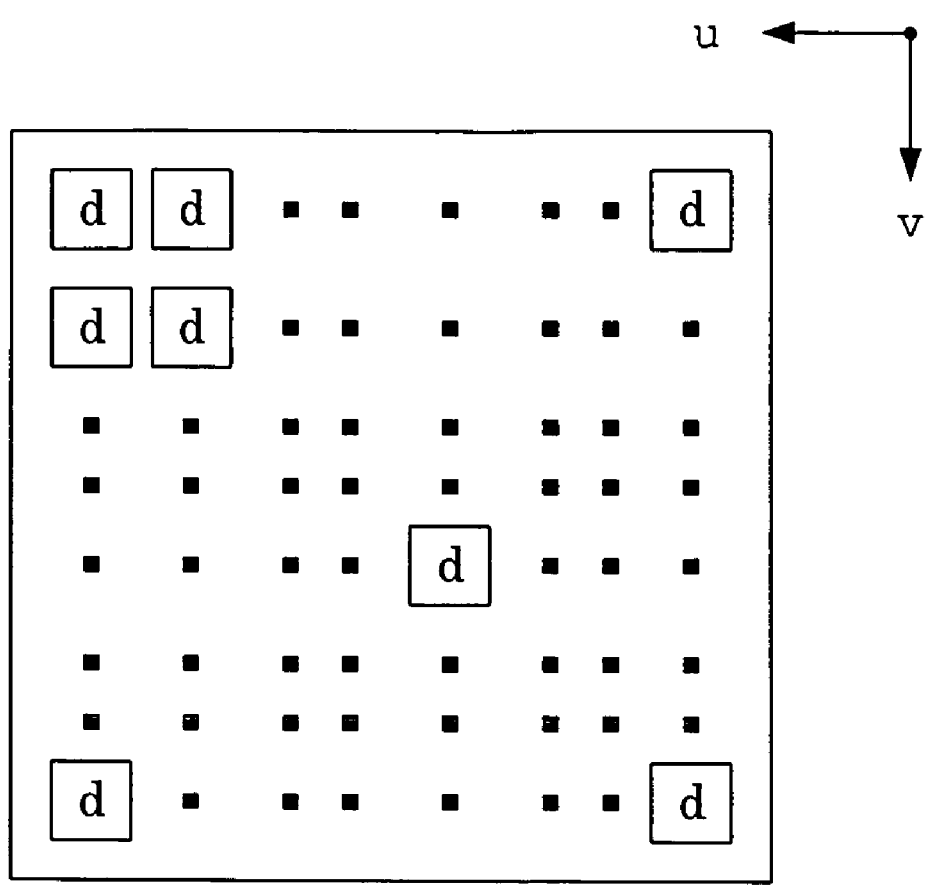
FIG. 5 is a schematic view of a detecting plane of an FPD.

FIG. 5 is a schematic view of the detecting plane of FPD 6. As shown in FIG. 5, the FPD 6 has a plurality of detecting elements d, sensitive to X rays, arranged in a matrix form on the detecting plane. For example, 1,536×1,536 detecting elements d are arranged on the detecting plane having an area about 30 cm long and 30 cm wide.

Here, for expediency, the rows of detecting elements d are regarded as extending along u-axis, and the columns of detecting elements d as extending along v-axis. The FPD 6 is supported by the FPD support member 39 to have the rows of detecting elements d extending in the direction (u-axis) parallel to the body axis A.

Figure 6:
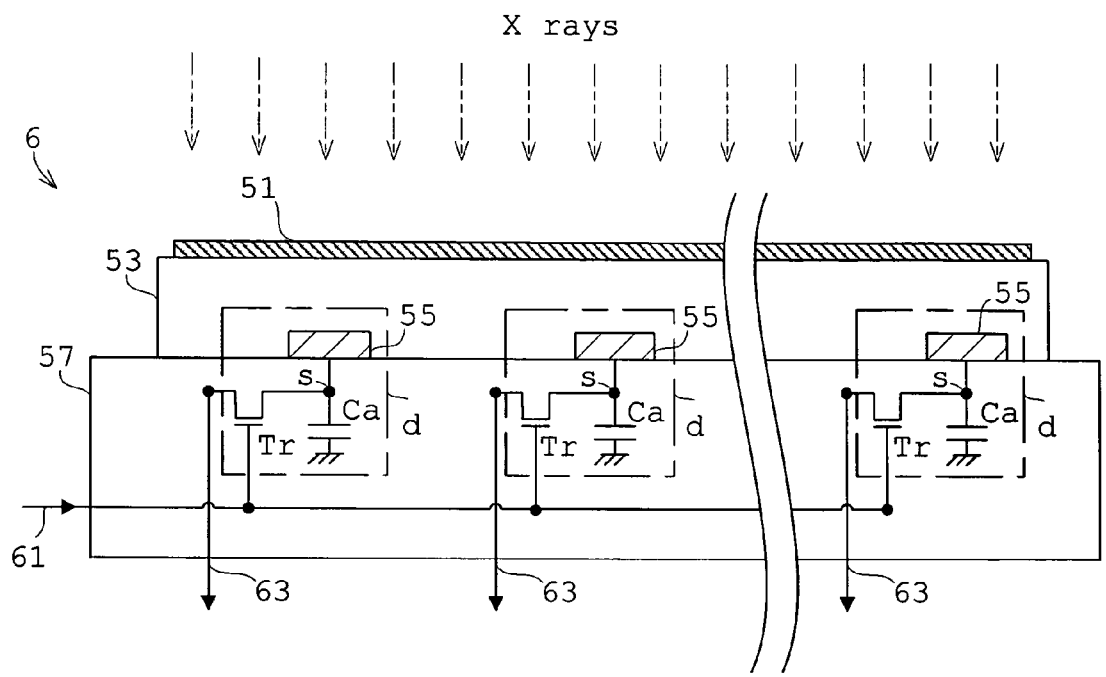
FIG. 6 is a view in vertical section of a principal part of the FPD.
Figure 7:
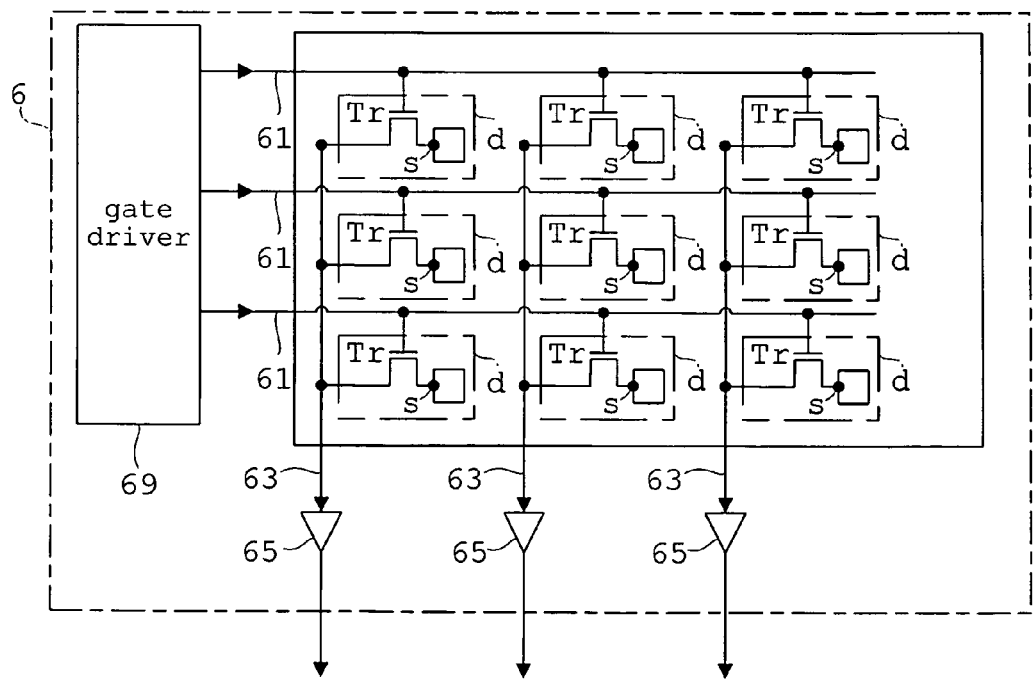
FIG. 7 is a plan view of the FPD.

The construction of FPD 6 will be described in greater detail with reference to FIGS. 6 and 7. FIG. 6 is a view in vertical section of a principal part of the FPD 6. FIG. 7 is a plan view of the FPD 6.

The FPD 6 has an application electrode 51, an X-ray sensitive semiconductor film 53, carrier collecting electrodes 55 and an active matrix substrate 57 laminated in order from the X-ray incidence side. That is, the FPD 6 is the direct conversion type that converts X rays directly into electric charges.

The semiconductor film 53 may be formed of amorphous selenium, for example. The active matrix substrate 57 may be a glass substrate having electrical insulation properties.

The carrier collecting electrodes 55 are arranged in a two-dimensional matrix form in plan view. Further, each carrier collecting electrode 55 has, formed on the active matrix substrate 57, a capacitor Ca for storing charge information, and a thin-film transistor Tr acting as a switching element with a source S thereof connected to the carrier collecting electrode 55 and capacitor Ca for fetching the charge information.

Each detecting element d is formed of one set of carrier collecting electrode 55, capacitor Ca and thin-film transistor Tr.

The active matrix substrate 57 has, laid thereon, gate bus lines 61 each for one row of detecting elements d, and data bus lines 63 each for one column of detecting elements d. Each gate bus line 61 is connected commonly to the gates of thin-film transistors Tr in one row. Each data bus line 63 is connected commonly to the drains of thin-film transistors Tr in one column.

The FPD 6 has a plurality of amplifiers 65 arranged at one end side of the active matrix substrate 57. A gate driver 69 is disposed at another end side of the active matrix substrate 57.

The data bus lines 63 are connected to the amplifiers 65, respectively. The gate bus lines 61 are connected to the gate driver 69. In addition, an analog-to-digital converter, not shown, is disposed at the output side of the amplifiers 65. The FPD 6 corresponds to the detecting device in this invention.

Operation of the FPD 6 will be described. When X rays impinge on the FPD 6, with a bias voltage applied to the application electrode 51, electric charges are generated in the semiconductor film 53. The electric charges are accumulated in the capacitors Ca through the respective carrier collecting electrodes 55. The gate bus lines 61 transmit scan signals from the gate driver 69 to the gates of thin-film transistors Tr. As a result, the thin-film transistors Tr are turned on to read the charge information from the capacitors Ca to the data bus lines 63. The charge information read through each data bus line 63 is amplified by the amplifier 65. Subsequently, the charge information is digitized by the analog-to-digital converter to provide detection signals. The detection signals are projection data for the positions of the detecting elements d, and are derived from actual detections.

The detection signals acquired from the FPD 6 in this way are applied to the image processing system 2. The image processing system 2 performs a reconstruction process based on a group of projection data received from the FPD 6, to obtain a three-dimensional sectional image. The image processing system 2 will particularly be described hereinafter.

The detection signal collecting unit 11 collects the detection signals from the FPD 6. The main memory 13 stores the detection signals.

The reconstruction processor 15 performs the reconstruction process based on the detection signals stored in the main memory 13, and creates sectional images. The cache memory 21 takes in and stores the detection signals from the main memory 13. Although the cache memory 21 has a smaller storage capacity than the main memory 13, the computing unit 23 can read the signals from the cache memory 21 at high speed. The computing unit 23 performs calculations necessary for the reconstruction process.

The storage unit 17 stores the sectional images obtained from the reconstruction processor 15. The sectional images are displayed on the display 3 in response to instructions given by the operator, for example.

The image processing system 2 includes a central processing unit (CPU) for reading and executing a predetermined program, a RAM (Random Access Memory) for storing varied information, and a storage medium such as a fixed disk. The image processing system 2 corresponds to the image processing device in this invention.

Next, operation of the radiographic apparatus in the first embodiment will be described as divided into the image pickup system 1, and the image processing system 2 and the display 3.

<Image Pickup System 1>

In the image pickup system 1, the roller 10 on the base 8 is rotated by the drive mechanism not shown, to drive the secondary scanning belt 9a. The frame holding member 9 and scan frame 7 are thereby rotated forward and backward together about the body axis A. In this way, the rotating anode X-ray tube 5 and FPD 6 in the scan frame 7 are moved to turn the sectional axis B on the body axis A. Such movement of the X-ray tube 5 and FPD 6 is called the secondary scanning.

In this embodiment, the sectional axis B is turned approximately 180 degrees around the body axis A.

In the scan frame 7, the rotary motor 31 rotates the rotary shaft 32. The rotary shaft 32 rotates the X-ray tube case 34 through the X-ray tube gear 33, and rotates the turntable 37 through the FPD gear 36.

With the rotation of the X-ray tube case 34, the rotating anode X-ray tube 5 mounted therein rotates about the sectional axis B. Further, with rotation of the high-speed rotary shaft 43 itself, the anode 42 of the X-ray tube 5 rotates about the axis of the high-speed rotary shaft 43.

On the other hand, the rotation of the turntable 37 moves the FPD support member 39 on a circular track with a radius corresponding to a distance of offset of the holding rod 37a relative to the sectional axis B. At this time, the back plate 39b of the FPD support member 39 contacts the holding frame 38 to restrict the FPD support member 39 to the fixed direction constantly. Therefore, the FPD support member 39 makes a parallel movement along the circular track.

The FPD 6 moves with the FPD support member 39 about the sectional axis B. Consequently, the FPD 6 makes a parallel movement on the circular track, while maintaining the rows of detecting elements d (u-axis) parallel to the body axis A.

In other words, the movement of the FPD 6 is a combination of a linear motion component m1 along the body axis A and a linear motion component m2 along an axis D perpendicular to the body axis A and sectional axis B.

Figure 8:
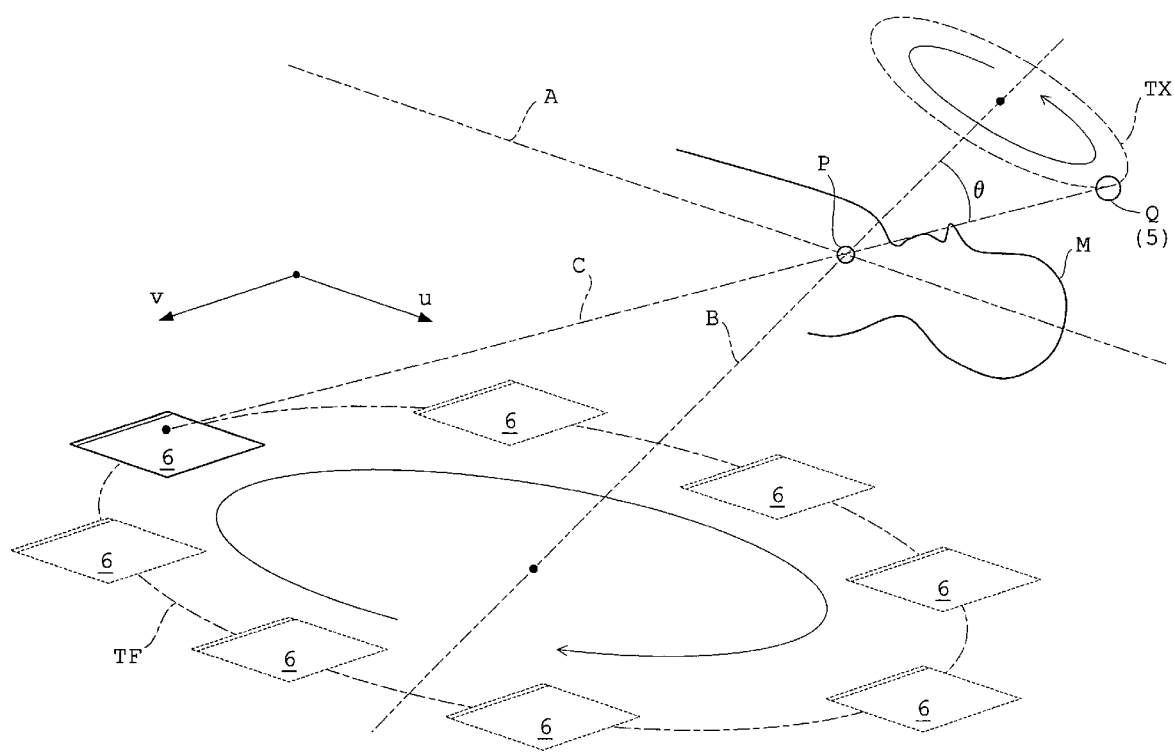
FIG. 8 is a schematic view showing a positional relationship between a rotating anode X-ray tube and the FPD in time of primary scanning.

FIG. 8 is a schematic view showing a positional relationship between the rotating anode X-ray tube and FPD 6 in the primary scanning. As shown in FIG. 8, the rotating anode X-ray tube 5 revolves on a circular track TX about the sectional axis B, while the FPD 6 moves on a circular track TF about the sectional axis B.

With the movement of the X-ray tube 5 and FPD 6, the radiation axis C linking the radiation source position Q of the X-ray tube 5 and the FPD 6 rotates about the sectional axis B while crossing the sectional axis B at a predetermined angle θ thereto at the site of interest P of the patient M. In this specification, such movement of the rotating anode X-ray tube 5 and FPD 6 is called the primary scanning.

The angle θ usually is 45 degrees or less. A preferred angle θ is 15 to 20 degrees.

In FIG. 8, one side of the detecting plane of the FPD 6 is schematically shown in a double line in order to clarify that the FPD 6 makes a parallel movement on the circular track TF.

In time of the secondary scanning, the FPD 6 revolves about the body axis A. Thus, also in the secondary scanning, the rows of detecting elements d (u-axis) are constantly parallel to the body axis A.

At each point of time in the primary scanning and secondary scanning of the image pickup system 1, the rotating anode X-ray tube 5 emits X rays to the patient M, and the FPD 6 detects X rays transmitted through the patient M. The detection signals acquired from the FPD 6 are applied to the image processing system 2.

<Image Processing System 2 and Display 3>

The detection signal collecting unit 11 collects detection signals acquired from the FPD 6 at varied points of time in the primary scanning and secondary scanning. The main memory 13 stores the detection signals collected by the detection signal collecting unit 11. The computing unit 23 of the reconstruction processor 15 performs a reconstruction process based on a group of detection signals, and creates sectional images. At this time, the cache memory 21 fetches from the main memory 13 beforehand detection signals required for the reconstruction process by the computing unit 23. The storage unit 17 stores the sectional images created by the reconstruction processor 15. The display 3 displays the sectional images stored in the storage unit 17.

Figure 9:
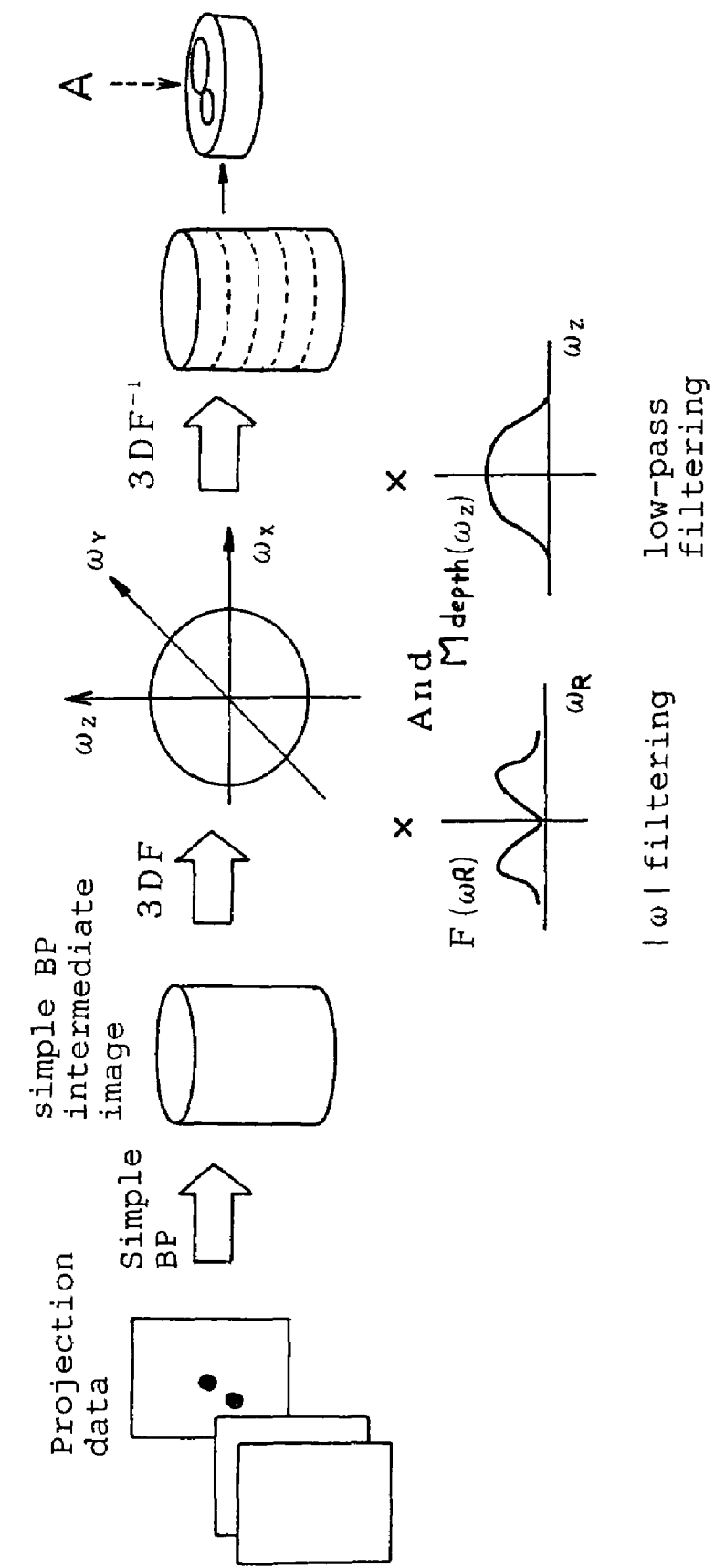
FIG. 9 is a schematic view illustrating a procedure of reconstruction process based on the primary scanning.
Figure 10:
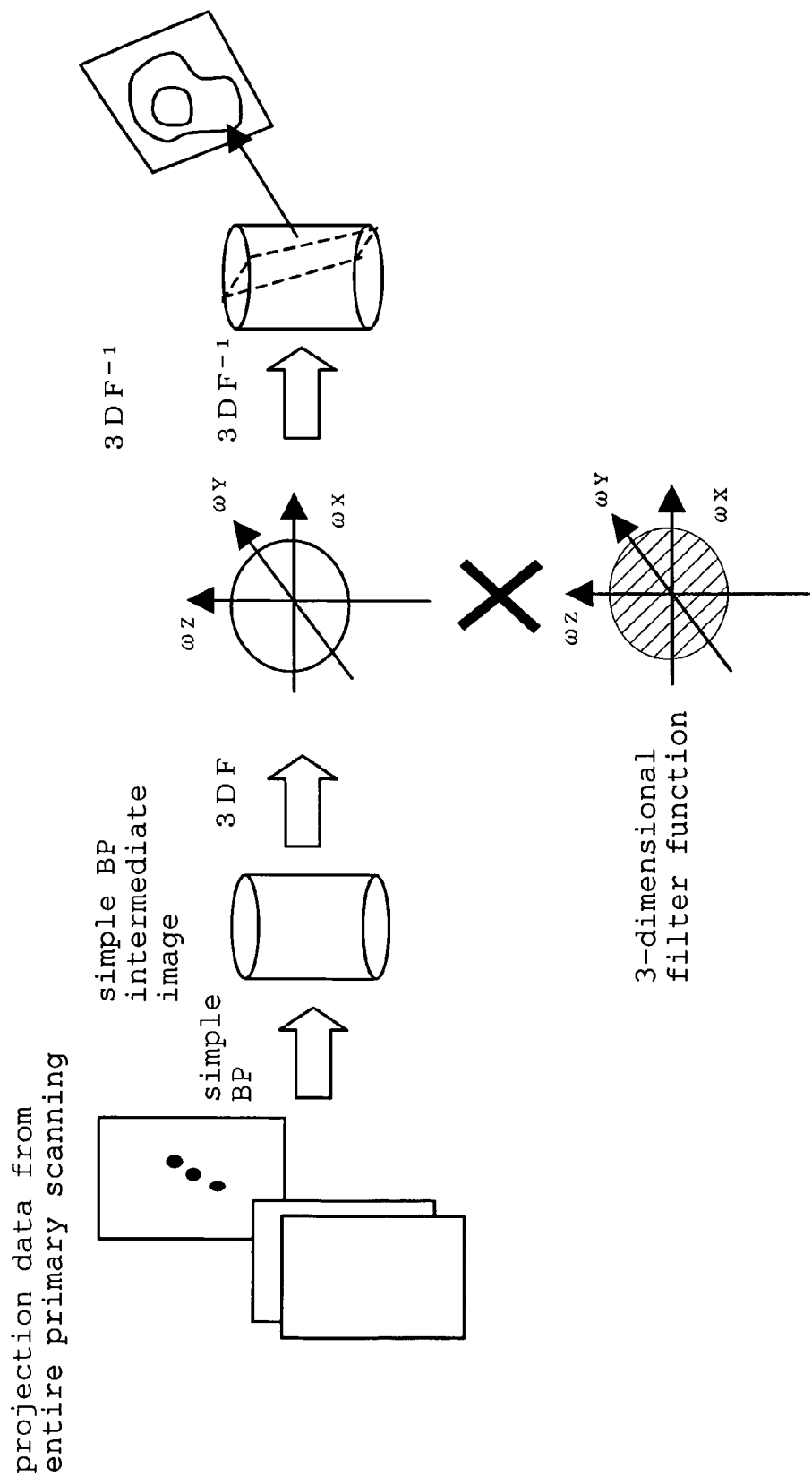
FIG. 10 is a schematic view illustrating a procedure of reconstruction process based on the primary scanning and secondary scanning.

Operation of the reconstruction processor 15 will now be described in detail, referring to FIGS. 9 and 10. FIG. 9 is a schematic view illustrating a procedure of reconstruction process based on the primary scanning. FIG. 10 is a schematic view illustrating a procedure of reconstruction process based on the primary scanning and secondary scanning.

First, the group of projection data is subjected to a simple back projection (simple BP) to create a simple BP intermediate image. Next, the simple BP intermediate image is subjected to a three-dimensional Fourier transform to create a three-dimensional Fourier distribution image which is Fourier space data converted from real space data (in FIGS. 9 and 10, the three-dimensional Fourier distribution image is shown in three-dimensional Fourier space coordinates). Next, the three-dimensional Fourier distribution image receives a filtering process (|ω| filtering (absolute value omega filtering) and low-pass filtering). Next, the three-dimensional Fourier distribution image filtered is subjected to a three-dimensional inverse Fourier transform to change the Fourier space data back to real space data and to create three-dimensional volume data (in FIGS. 9 and 10, this corresponds to the cylindrical object shown toward the right-hand end, with several dotted lines extending circumferentially). The image reconstruction is carried out in this way to create three-dimensional volume data of the site of interest P. The operator may observe an image of any slice plane selected from the three-dimensional volume data (in FIGS. 9 and 10, this corresponds to the thin cylindrical object shown at the extreme right-hand end). As noted above, a simple BP intermediate image is created once, and a predetermined filtering process is carried out for the simple BP intermediate image in the Fourier space. This procedure is called an F (Fourier) space filter method.

When a reconstruction process is performed based on the primary scanning and secondary scanning (which corresponds to the procedure shown in FIG. 10), high resolution is secured in the direction of the sectional axis B, thereby to obtain sectional images with isotropic spatial resolution of the patient.

Generation of the simple BP intermediate image will be described in greater detail.

Figure 11:
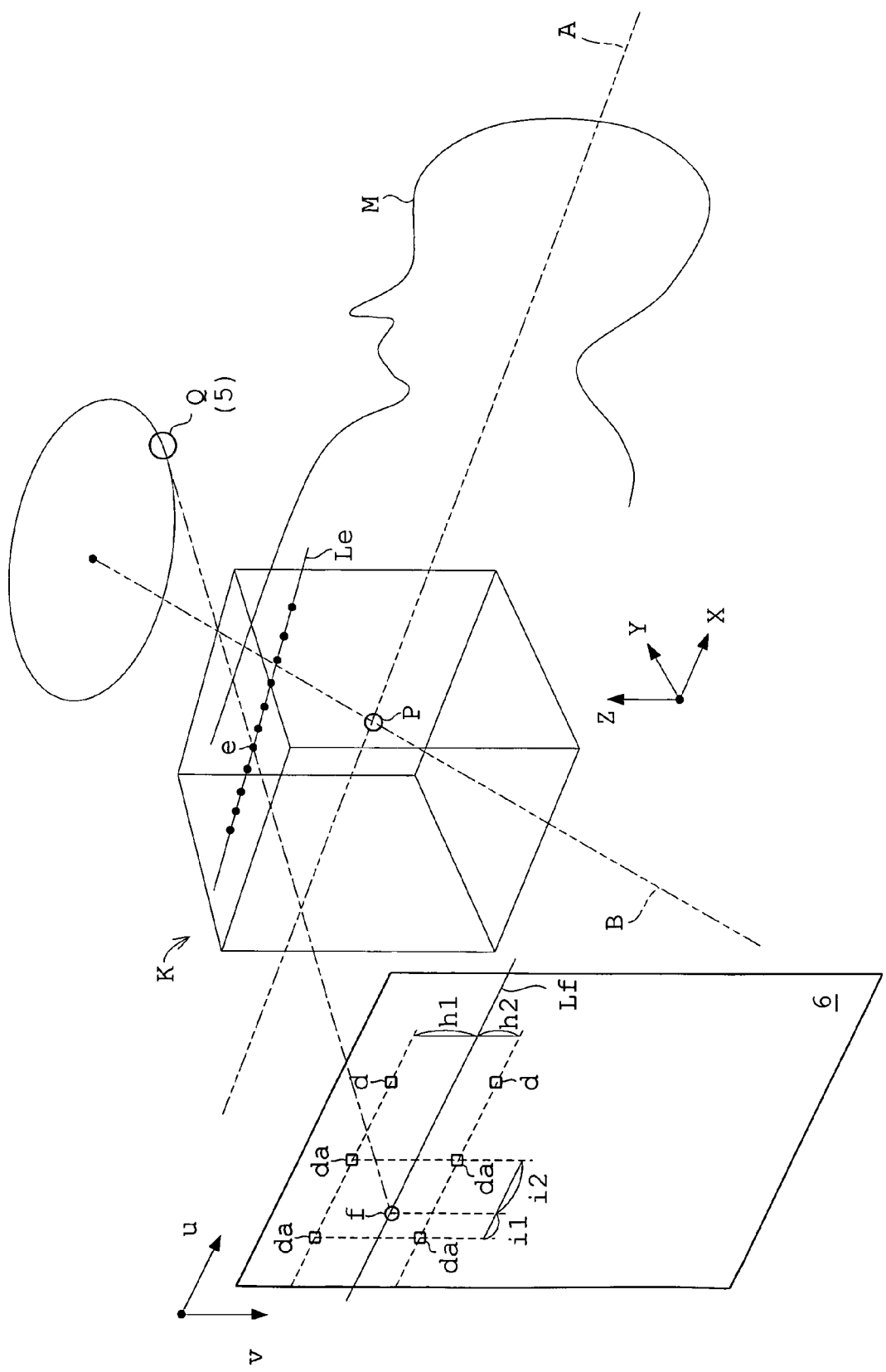
FIG. 11 is a schematic view illustrating a back projection method.

As shown in FIG. 11, a three-dimensional lattice K is virtually set to the radiographed site of interest P of the patient M. For example, the three-dimensional lattice K has 1,000 virtual lattice points arranged in each of X-axis, Y-axis and Z-axis directions in FIG. 11. The three-dimensional lattice K is set to have one of the three axes parallel to the body axis A. In FIG. 11, the X-axis is parallel to the body axis A.

Next, projection data is determined for each point (hereinafter called "projection point") on the detecting plane of the FPD 6 to which each lattice point of the three-dimensional lattice K is projected. In this embodiment, projection data at each projection point is determined by obtaining a weighted mean of detection signals acquired from a plurality of detecting elements d closest to the projection point.

Specifically, projection data at projection point f of lattice point e is determined by obtaining a weighted means of the detection signals acquired from four detecting elements da closest to the projection point f, based on a positional relationship between projection point f and each detecting element da. The positional relationship can be specified by a positional relationship (h1, h2) in the u-axis direction and a positional relationship (i1, i2) in the v-axis direction in the u-v coordinate system.

When obtaining projection data for each projection point, the cache memory 21 fetches at least the detection signals of the detecting elements closest to the projection point from the main memory 13. The computing unit 23 will perform data processing to obtain projection data for each projection data.

The projection data obtained for each projection point is projected back to the lattice point e. Such projection data is obtained from various angles and accumulated on the lattice point to create a simple BP intermediate image for this lattice point. A similar back projection is carried out for the remaining lattice points of the three-dimensional lattice K. Further, this back projection is carried out for the varied points of time in the primary scanning and secondary scanning, thereby to create simple BP intermediate images with isotropic spatial resolution. A blur preventive filtering process may be applied to radiographic images of the patient M beforehand.

Here, projection points of other lattice points arranged with the lattice point e in the direction of the body axis A (on straight line Le in FIG. 11) are considered. Since the straight line Le extends in the direction of the body axis A, it is parallel also to the u-axis. Thus, the other projection points are distributed on a straight line Lf parallel to the u-axis.

Therefore, the projection data projected back to the lattice points in one row in the direction of the body axis A is derived only from the detection signals acquired from the detecting elements d on the two lines at opposite sides of the straight line Lf.

Thus, for performing a back projection to the lattice points in one row in the direction of the body axis A, the cache memory 21 needs to fetch only the detection signals for these two lines from the main memory 13.

The positional relationship (h1, h2) in the u-axis direction between each projection point and the plurality of detecting elements d closest to the projection point is the same throughout. The positional relationship (i1, i2) in the v-axis direction varies for each lattice point.

The computing unit 23 can determine a positional relationship of each projection point by carrying out calculations for the positional relationship in the u-axis direction only once, and calculations for the positional relationship in the v-axis direction the number of times corresponding to the number of projection points.

Thus, according to the radiographic apparatus in the first embodiment, since the direction of arrangement (u-axis) of the detecting elements d is constantly parallel to the body axis A in time of the primary scanning and secondary scanning, the quantity of detection signals taken into the cache memory 21 may be reduced to a minimum for the process of back projection to the lattice points in one row in the direction of the body axis A. Consequently, the frequency of accessing the main memory 13 is reduced to shorten the time required for accessing.

In the process of back projection to the lattice points in one row in the direction of the body axis A, the computing unit 23 can largely dispense with the calculating process for determining a positional relationship in the u-axis direction of the projection point of each lattice point. Consequently, the time required for the processing by the computing unit 23 is reduced.

As a result, the reconstruction processor 15 can create a three-dimensional sectional image at increased speed (i.e. in a reduced time).

This feature enables the invention to be applied to a four-dimensional radiographic apparatus (4DCT) for providing sectional images in real time. It is also possible to grasp variations with time in dynamic sectional images, for example.

The base 8 itself may have a compact construction in that, in time of the secondary scanning, the base 8 rotates the frame holding member 9 while holding a part thereof. This reduces the floor area occupied by the entire radiographic apparatus. An open space above the patient M gives a feeling of openness to the patient M.

The high-speed rotary shaft 43 of the rotating anode X-ray tube 5 is constantly parallel to the sectional axis B in time of the primary scanning. This reduces a force acting on the bearing 44 during a revolution about the sectional axis B, to prevent damage to the bearing 44.

With the length FS of one side of the FPD 6 having a value derived from equation (1), the detection signals may be used for the reconstruction process without waste. That is, the turning diameter (2XR) of the radiation source position Q of the X-ray tube 5 is equal to one side of a center plane of the three-dimensional lattice K virtually set to the site of interest P of the patient M (hereinafter called "center plane of the reconstruction area of interest"). In FIG. 11, the center plane of the reconstruction area of interest is parallel to the X-axis and Z-axis of the three-dimensional lattice K, and corresponds to a plane including the site of interest P of the patient M. Therefore, when the detecting plane is square with one side of the detecting plane exactly 2XR×SD/SO, the size of the detecting plane is equal to the size of the entire projection image of X rays through the center plane of the reconstruction area of interest. Thus, there is no possibility of acquiring detection signals not required to obtain sectional images with respect to the center plane of the reconstruction area of interest. All the acquired detection signals are used for sectional images without being wasted.

The counterbalance 37b attached to the turntable 37 can prevent the inconvenience of the turntable 37 vibrating during rotation.

With the X-ray tube gear 33 and FPD gear 36 equal in diameter and connected to the rotary shaft 32, the rotating anode X-ray tube 5 and FPD 6 can easily be rotated synchronously.

Second Embodiment

Figure 12:
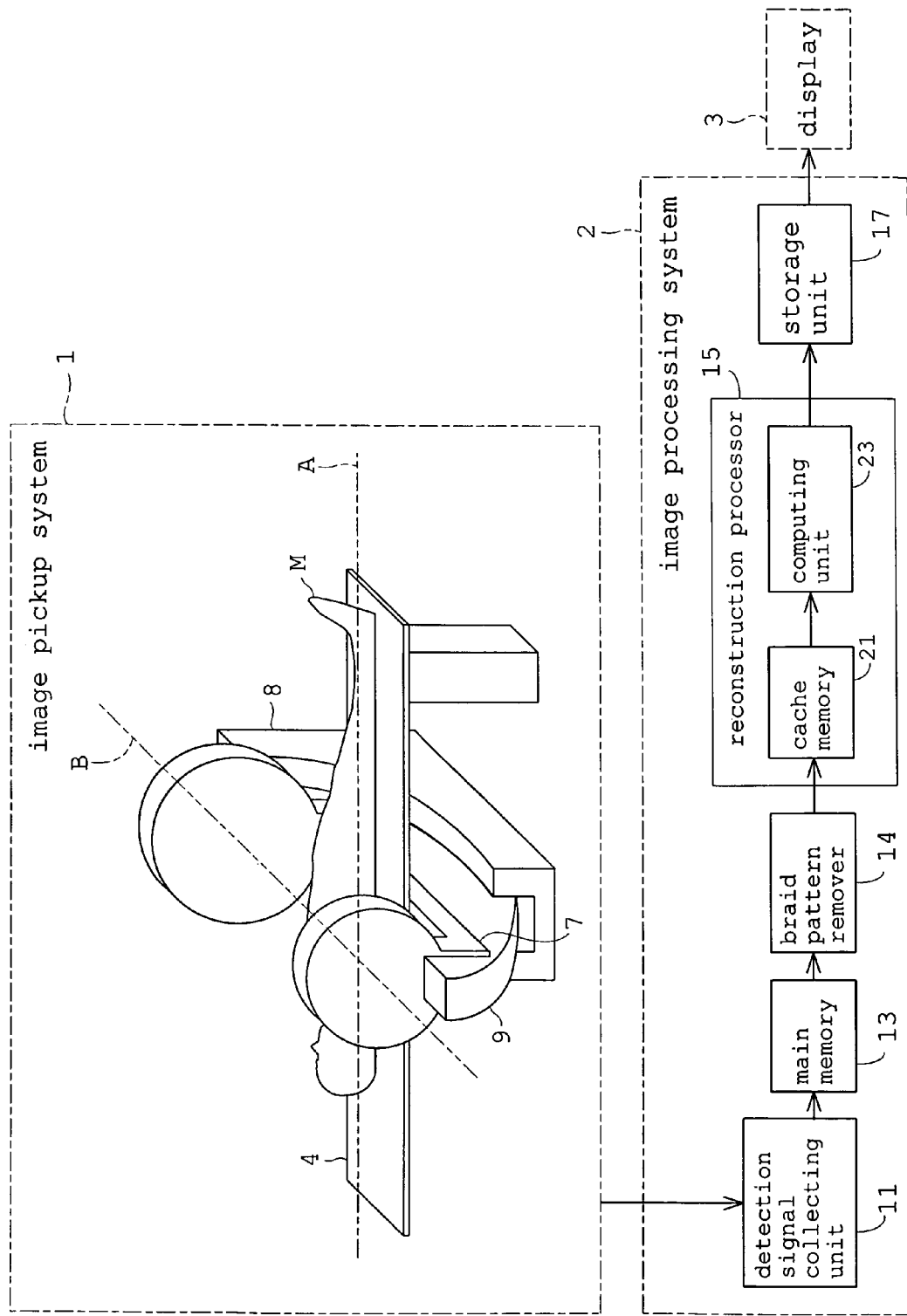
FIG. 12 is a block diagram showing an outline of a radiographic apparatus in a second embodiment.
Figure 13:
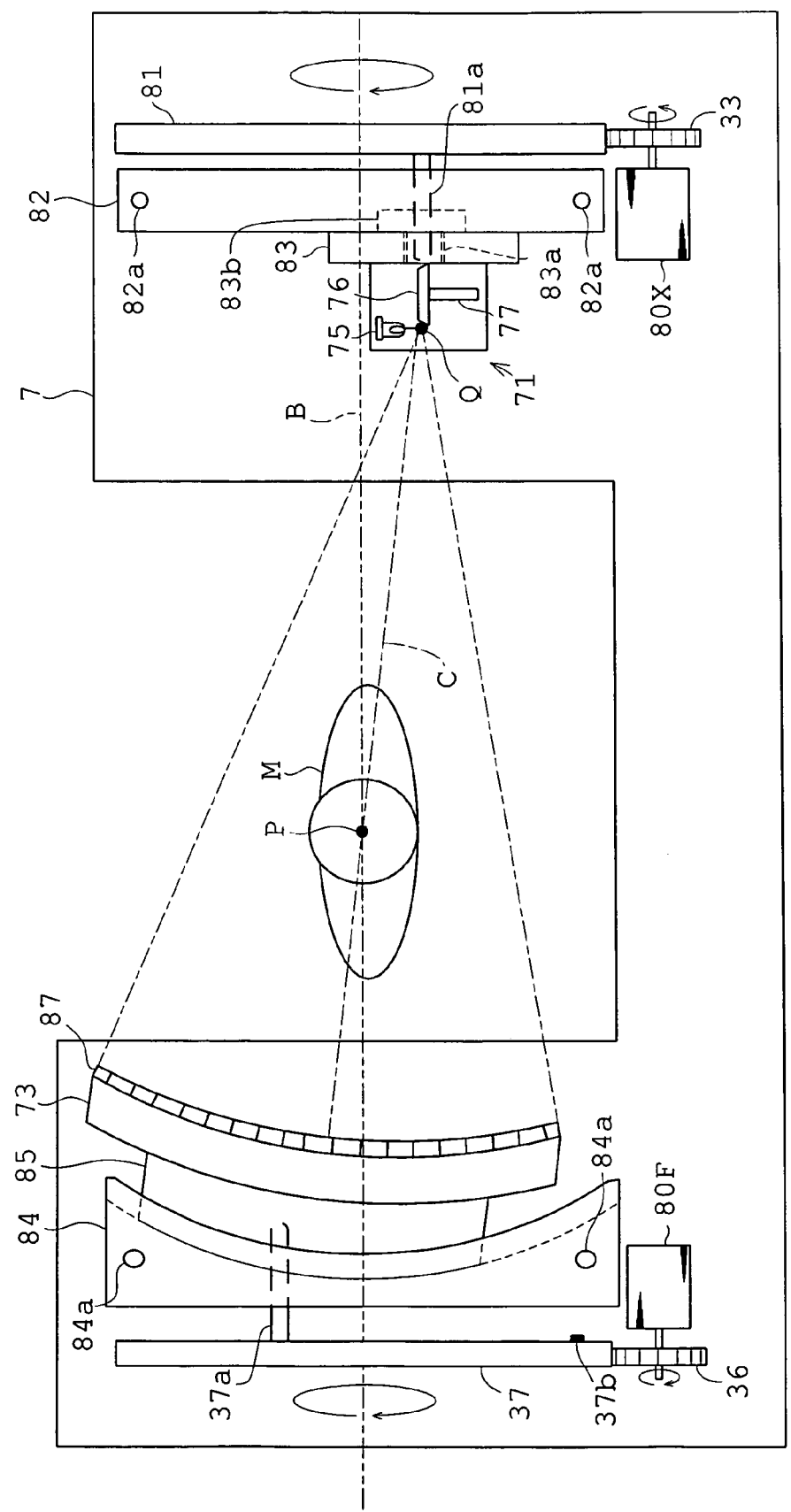
FIG. 13 is a sectional side view of a scan frame.
Figure 14:
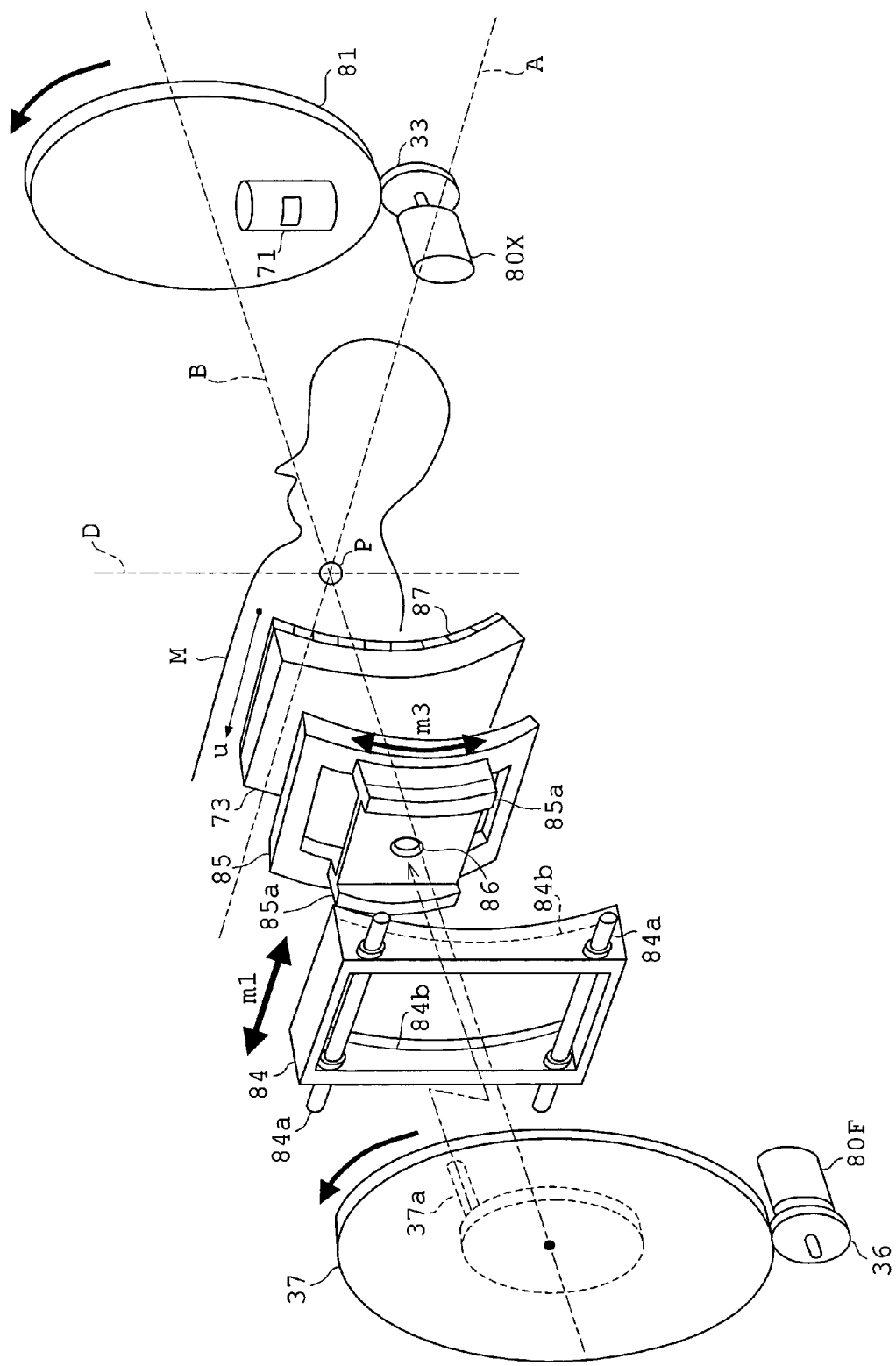
FIG. 14 is a perspective view of an interior of the scan frame.
Figure 15:
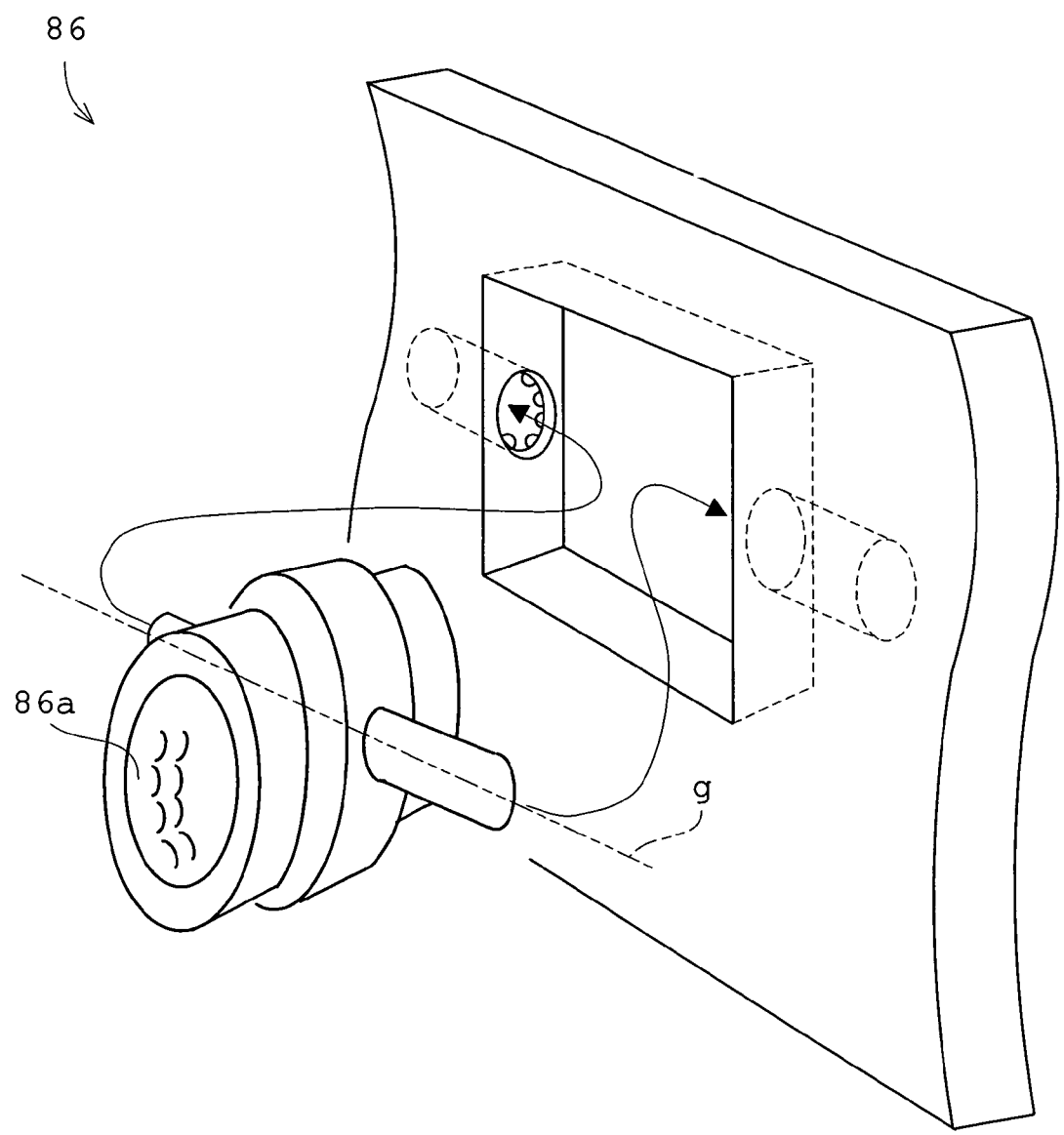
FIG. 15 is a perspective view of a rotary type linear bearing of an FPD support member.

A second embodiment of this invention will be described hereinafter with reference to the drawings. Like reference numerals are used to identify like parts which are the same as in the first embodiment and will not be described again. FIG. 12 is a block diagram showing an outline of a radiographic apparatus in the second embodiment. FIG. 13 is a sectional view of a scan frame taken on a sectional axis. FIG. 14 is a perspective view of an interior of the scan frame. FIG. 15 is a perspective view of a rotary linear bearing of an FPD support member.

The image processing system 2 includes a detection signal collecting unit 11, a man memory 13, a braid pattern remover 14, a reconstruction processor 15 and a storage unit 17. The reconstruction processor 15 has a cache memory 21 and a computing unit 23.

Each component will be described hereinafter.

As shown in FIGS. 13 and 14, the scan frame 7 houses, besides a rotating anode X-ray tube 71 and an FPD 73, an X-ray tube rotating motor 80X, an X-ray tube gear 33, an X-ray tube turntable 81, an X-ray tube holding frame 82, an X-ray tube support member 83, an FPD rotating motor 80F, an FPD gear 36, a turntable 37, a holding frame 84 and an FPD support member 85. An FPD 73 has a braid 87 disposed on the detecting plane thereof.

The second embodiment provides the separate X-ray tube rotating motor 80X and FPD rotating motor 80F. These X-ray tube rotating motor 80X and FPD rotating motor 80F are synchronously rotatable under digital control by a controller not shown.

The X-ray tube rotating motor 80X is connected to the X-ray tube turntable 81 through the X-ray tube gear 33. The X-ray tube turntable 81 is rotatable about the sectional axis B. The FPD rotating motor 80F is connected to the turntable 37 through the FPD gear 36. The turntable 37 is rotatable about the sectional axis B.

The X-ray tube turntable 81 has a holding rod 81a in a position offset from its center. The X-ray tube holding frame 82 has four sides, and the X-ray tube holding rod 81a extends through an opening formed in the holding frame 82. This holding frame 82 has two frame holding rods 82a extending through two opposite sides, and parallel to the body axis A. These frame holding rods 82a are fixed to the scan frame 7. The X-ray tube holding frame 82 has bearings in positions thereof penetrated by the frame holding rods 82a, respectively, to be slidable only in directions along the body axis A.

The X-ray tube support member 83 has a bearing 83a defining a bore with a rotatable inner peripheral surface. The X-ray tube support member 83 is held by the X-ray tube turntable 81, with the bearing 83a joined with the holding rod 81a. The X-ray tube support member 83 has a back plate 83b attached to the back thereof for contacting the inside of the X-ray tube holding frame 82, so that the X-ray tube support member 83 constantly face a fixed direction. Further, the X-ray tube support member 83 supports the rotating anode X-ray tube 71 in a predetermined position, so that the X-ray tube 71 emit X rays to irradiate the site of interest P of the patient M with rotation of the X-ray tube turntable 81.

The rotating anode X-ray tube 71 includes a cathode (filament) 75 for releasing thermions, an anode (target) 76 for generating X rays by accelerated collision with the thermions from the cathode 75, a high-speed rotary shaft 77 for rotating the anode 76 at high speed about its center, and a bearing (not shown) for rotatably supporting the high-speed rotary shaft 77. The rotating anode X-ray tube 71 corresponds to the radiation source in this invention.

The rotating anode X-ray tube 71 has the cathode 75 and anode 76 arranged in a different relative position to the rotating anode X-ray tube 5 in the first embodiment. The high-speed rotary shaft 77 of the X-ray tube 71 extends perpendicular to the sectional axis B.

The turntable 37 has a holding rod 37a in a position offset from its center. The holding frame 84 has four sides, and the holding rod 37a extends through an opening formed in the holding frame 84. The FPD support member 85 is held by the holding rod 37a through the holding frame 84.

The holding frame 84 has two frame holding rods 84a extending through two opposite sides thereof. The two frame holding rods 84a are parallel to the body axis A, and are fixed to the scan frame 7. The holding frame 84 has bearings having rotatable inner surfaces and disposed in positions of the two sides thereof penetrated by the frame holding rods 84a, respectively. Thus, the holding frame 84 is movable along the frame holding rods 84a (i.e. along the body axis A). Further, the holding frame 84 has guide grooves 84b formed in inner walls of the two sides to extend along concentric circles about the body axis A as seen in section.

As shown in FIG. 15, the FPD support member 85 has, in a substantially central part thereof, a rotary type linear bearing 86 rotatable in two directions. The rotary type linear bearing 86 includes a bore having a rotatable inner peripheral surface 86a, the bore itself being rotatable about an axis g. The FPD support member 85 is held by the turntable 37, with the rotary type linear bearing 86 joined with the holding rod 37a.

The FPD support member 85 has two back plates 85a projecting from the back thereof. The back plates 85a are curved to extend along concentric circles about the body axis A. With the rotary type linear bearing 86 joined with holding rod 37a, the back plates 85a are in slidable contact with the guide grooves 84b formed in the inner walls of the holding frame 84.

The FPD support member 85 supports the FPD 73 to be opposed to the rotating anode X-ray tube 71 across the patient M.

The X-ray tube rotating motor 80X, FPD rotating motor 80F, X-ray tube gear 33, X-ray tube turntable 81, X-ray tube support member 83, FPD gear 36, turntable 37, holding frame 84 and FPD support member 85 constitute the primary scanning device in this invention.

As shown in FIG. 14, the detecting plane of the FPD 73 is a curve plane uniform in the u-axis direction. Detecting elements d are arranged in a matrix form on the curved detecting plane. Each row of detecting elements d is parallel to the u-axis although this detecting plane cannot be regarded as two-dimensional coordinates as can the detecting plane in the first embodiment. The FPD 73 is supported by the FPD support member 85 so that the rows of detecting elements d (u-axis) are parallel to the body axis A. The FPD 73 corresponds to the detecting device in this invention.

The braid 87 is disposed on the detecting plane of FPD 73 for removing scattered X rays. The braid 87 includes a plurality of shields extending parallel to the rows of detecting elements d (u-axis). Each shield is inclined to point toward the radiation source position Q of the rotating anode X-ray tube 71. The shields may be formed of molybdenum or tungsten, for example.

The other aspects of the FPD 73 are the same as in the first embodiment. The FPD 73 corresponds to the detecting device in this invention.

The image processing system 2 will be described hereinafter only in relation to the braid pattern remover 14.

The braid pattern remover 14 removes reflections of the shields of the braid 87 (hereinafter called "braid pattern components") from the detection signals stored in the main memory 13.

The braid pattern remover 14 also includes a central processing unit (CPU) for reading and executing a predetermined program, a RAM (Random Access Memory) for storing varied information, and a storage medium such as a fixed disk.

Next, operation of the radiographic apparatus in the second embodiment will be described as divided into the image pickup system 1, and the image processing system 2 and display 3.

<Image Pickup System 1>

The image pickup system 1 performs the same secondary scanning as in the first embodiment. The primary scanning will be described hereinafter.

In the scan frame 7, the X-ray tube and FPD rotating motors 80X and 80F are driven under synchronous control of the controller not shown. The X-ray tube rotating motor 80X rotates the X-ray tube table 81 through the X-ray tube gear 33. The FPD rotating motor 80F rotates the turntable 37 through the FPD gear 36.

With the rotation of the X-ray tube table 81, the X-ray tube support member 83 moves on a circular track with a radius corresponding to a distance the holding rod 81a is offset from the sectional axis B. At this time, the back plate 83b of the X-ray tube support member 83 contacts the X-ray tube holding frame 82, whereby the X-ray tube support member 83 constantly faces the fixed direction. Consequently, the X-ray tube support member 83 makes a parallel movement along the circular track.

The rotating anode X-ray tube 71 moves with this X-ray tube support member 83 about the sectional axis B. Thus, the X-ray tube 71 also makes a parallel movement along a circular track without changing its posture. Further, with rotation of the high-speed rotary shaft 77 itself, the anode 76 of the X-ray tube 71 rotates about its center.

On the other hand, with rotation of the turntable 81, the FPD support member 85 moves on a circular track with a radius corresponding to a distance the holding rod 37a is offset from the sectional axis B. At this time, the back plates 85a of the FPD support member 85 are in contact with the inner walls of the holding frame 84. The holding frame 84 thereby restrains the FPD support member 85 itself from rotating about the rotary type linear bearing 86 (i.e. about the axis of the holding rod 37a). Further, with revolution of the holding rod 37a, the back plates 85a slide along the guide grooves 84b of the holding frame 84. As a result, the FPD support member 85 moves forward and backward along an arc of a circle about the body axis A. The FPD 73 moves with the FPD support member 85.

More particularly, the FPD 73 makes a rotational movement along an arc (circumference) about the body axis A when moved in the direction of an axis (hereinafter called the "third axis") D extending perpendicular to the body axis A and sectional axis B. That is, the movement of the FPD 73 is a combination of a linear motion component m1 along the body axis A and a rotational motion component m3 along the arc about the body axis A.

Figure 16:
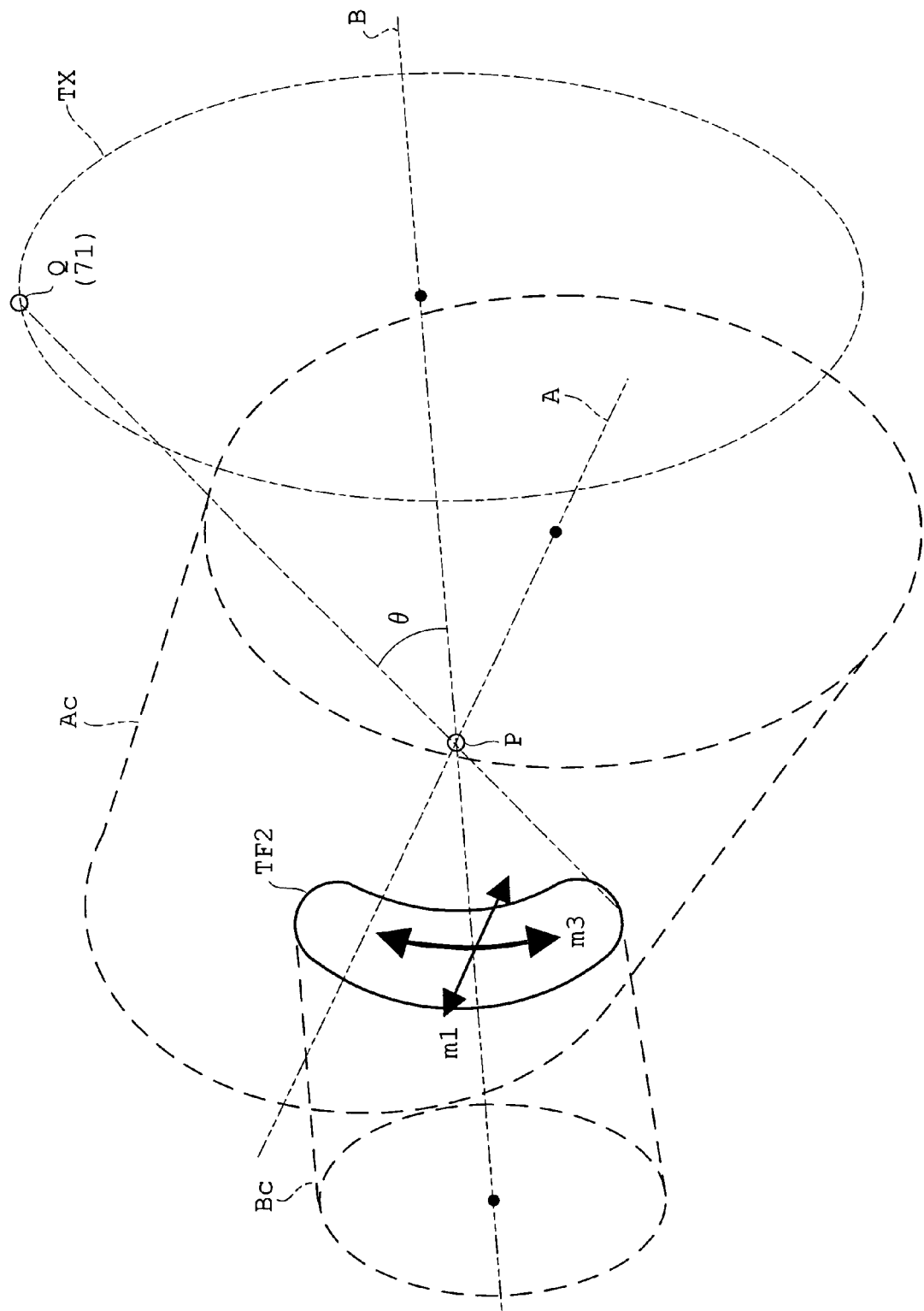
FIG. 16 is a schematic view showing a positional relationship between a rotating anode X-ray tube and the FPD in time of primary scanning in the second embodiment.

The FPD 73 may be seen from a different point of view as follows. FIG. 16 is a schematic view showing a positional relationship in time of the main scanning between the rotating anode X-ray tube and FPD in the second embodiment. As shown in FIG. 16, the FPD 73 is movable along a curve TF2 (also called a saddle type) linking intersections of a virtual cylinder Ac about the body axis A and a virtual cylinder Bc about the sectional axis B. The detecting plane of the FPD 73 inclines to be in constant contact with the cylinder Ac.

With the above movement of the rotating anode X-ray tube 71 and FPD 73, the radiation axis C extending between the radiation source position Q of the X-ray tube 71 and the FPD 73 revolves about the sectional axis B while crossing the sectional axis B at a predetermined angle θ at the site of interest P of the patient M. That is, such movement of the X-ray tube 71 and FPD 73 is the main scanning.

Although the inclined posture of the detecting plane of the FPD 73 changes in time of the main scanning, this is based only on the rotational motion component m3 along the circle about the body axis A. Thus, the rows of detecting elements d (u-axis) are constantly maintained parallel to the body axis A.

The braid 87 is movable with the FPD 73. The movement of the braid 87 also is a combination of the linear motion component m1 along the body axis A and the rotational motion component m3 along the arc about the body axis A. Since the linear motion component m1 along the body axis A is movement in the direction of arrangement of the shields, the shields remain facing the rotating anode X-ray tube 71. With the rotational motion component m3 along the arc about the body axis A, the braid 87 inclines to be in contact with the cylinder Ac. Consequently, each shield of the braid 87 always turns to the radiation source position Q of the rotating anode X-ray tube 71. In time of the primary scanning, therefore, each shield of the braid 87 is constantly turned to the radiation source position Q of the rotating anode X-ray tube 71.

In time of the secondary scanning, the FPD 73 will rotate about the body axis A. Thus, in the secondary scanning also, the rows of detecting elements d (u-axis) are constantly parallel to the body axis A. Each shield of the braid 87 constantly faces the rotating anode X-ray tube 71 in time of the second scanning also.

At each point of time in the primary scanning and secondary scanning of the image pickup system 1, the rotating anode X-ray tube 71 emits X rays to the patient M, and the FPD 73 detects X rays transmitted through the patient M. The detection signals acquired from the FPD 73 are applied to the image processing system 2.

<Image Processing System 2 and Display 3>

Operation of the reconstruction processor 15 and others is the same as in the first embodiment 1. Operation of the braid pattern remover 14 will be described hereinafter.

Pattern components of the braid 87 are extracted from detection signals for one frame by FIR (Finite Impulse Response) filtering, for example. The extracted pattern components of the braid 87 are remedied with surrounding detection signals. A two-dimensional Fourier transform is a specific example used for extracting pattern components of the braid 87.

Thus, with the radiographic apparatus in the second embodiment also, the direction of arrangement (u-axis) of the detecting elements d is constantly parallel to the body axis A in time of the primary scanning and secondary scanning. The reconstruction processor 15 can create sectional images at increased speed (i.e. in a reduced time).

The high-speed rotary shaft 77 of the rotating anode X-ray tube 71 lies in the same direction in time of the primary scanning. This reduces a force acting on the bearing (not shown) to prevent damage to the bearing. Compared with the case of the X-ray tube fixed to the X-ray tube table 87, with the high-speed rotary shaft 77 rotatable with the turntable 81, the second embodiment has an advantage of reducing a force acting on the bearing.

As noted hereinbefore, the movement of the FPD 73 is a combination of the linear motion component m1 along the body axis A and the rotational motion component m3 along the arc about the body axis A. Consequently, the detecting plane is inclined to face the rotating anode X-ray tube 71 while constantly maintaining the direction of arrangement of the detecting elements d (u-axis) parallel to the body axis A.

The braid 87 disposed on the detecting plane can effectively remove scattered X rays. Since each shield is constantly turned toward the rotating anode X-ray tube 71 during the primary scanning, X rays are not unnecessarily blocked by the shields.

X-ray incidence in the direction of the rows (u-axis) is little blocked since the shields of the braid 87 are arranged in the direction of arrangement of the detecting elements d (u-axis) parallel to the body axis A. The quantity blocked by the braid 87 is invariable in each position of the FPD 73 during the primary scanning. This facilitates removal of the pattern components of the braid 87, and allows the subsequent reconstruction process to be carried out advantageously.

The rotary shaft 32 may be omitted by providing the separate rotary motors 80X and 80F for the X-ray tube and FPD. This increases freedom for the shape of the scan frame 7.

This invention is not limited to the foregoing embodiments, but may be modified as follows:

(1) In the first embodiment described hereinbefore, the rows of detecting elements d (u-axis) are constantly maintained parallel to the body axis A in time of the primary scanning and secondary scanning. Here, the rows are "parallel" enough as long as each projection point of the lattice points arranged along the body axis A fits between two rows of detecting elements d. Such a case also is included in the meaning of "parallel".

(2) In the first embodiment described hereinbefore, the rows of detecting elements d (u-axis) are constantly maintained parallel to the body axis A in time of the primary scanning and secondary scanning. This is not limitative. For example, the columns of detecting elements d (v-axis) may be constantly maintained parallel to the body axis A.

Figure 17:
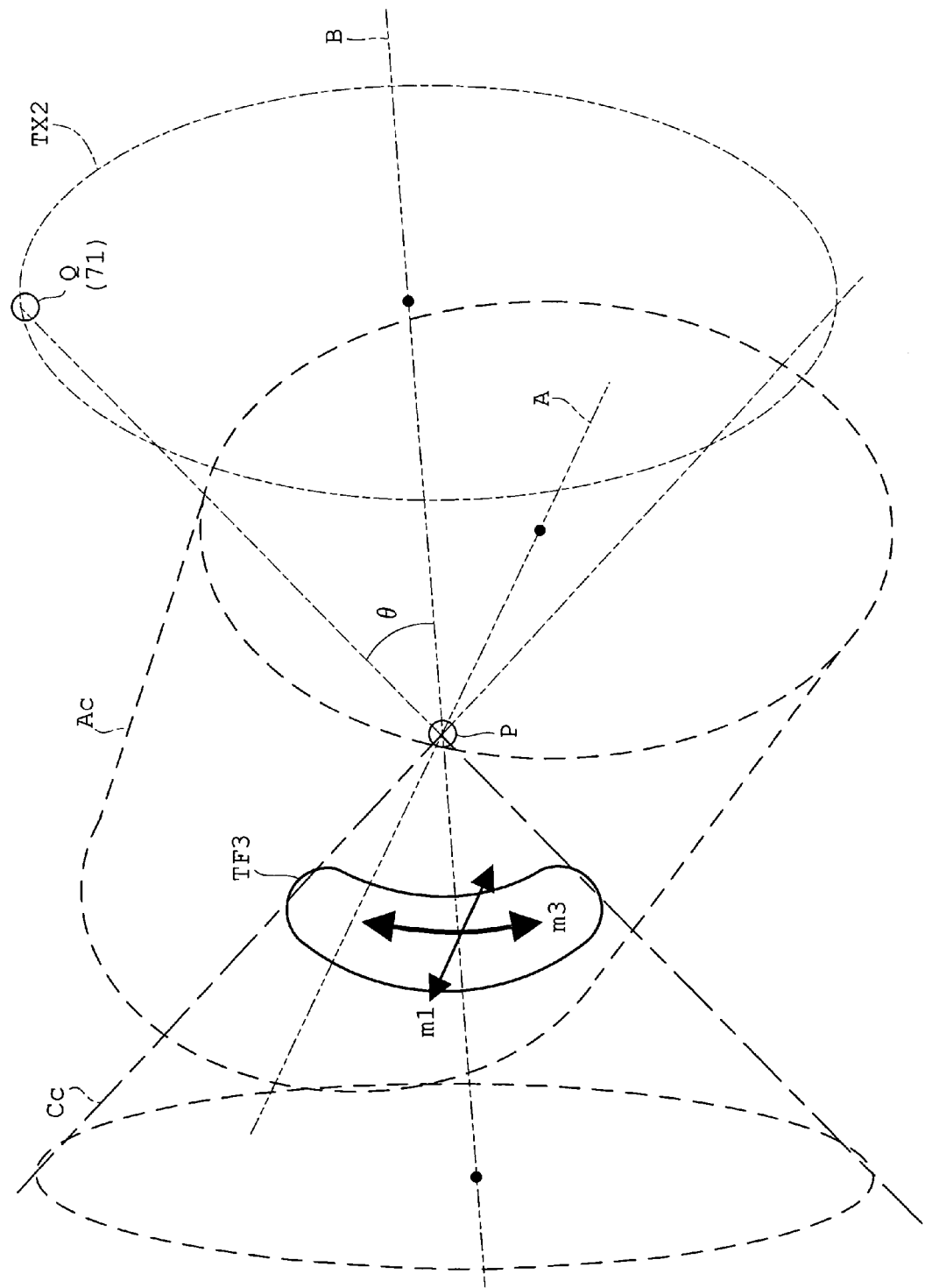
FIG. 17 is a schematic view showing a positional relationship between rotating anode X-ray tube and FPD in time of primary scanning in a modified embodiment.

(3) In the second embodiment described hereinbefore, the FPD 73 is movable along the curve TF2 linking intersections of the virtual cylinder Ac about the body axis A and the virtual cylinder Bc about the sectional axis B. This is not limitative. As shown in FIG. 17, for example, the FPD 73 may be moved along a curve TF3 linking intersections of the virtual cylinder Ac about the body axis A and a virtual cone Cc formed at a predetermined angle θ about the sectional axis B, with an intersection of the body axis A and sectional axis B (the site of interest P of the patient M) providing its apex.

In addition, the FPD 73 may be moved along any curve as long as the rows of detecting elements d (u-axis) are constantly maintained parallel to the body axis A in time of the primary scanning and secondary scanning.

For example, a stepping motor having a rotary shaft parallel to the body axis A may be provided on the front face of the FPD support member 39 in the first embodiment, with the FPD 6 (73) rotatably supported by the stepping motor. With this construction, the detecting plane may be inclined while moving the FPD 6 (73) on a circular track in one plane perpendicular to the sectional axis B.

Figure 18:
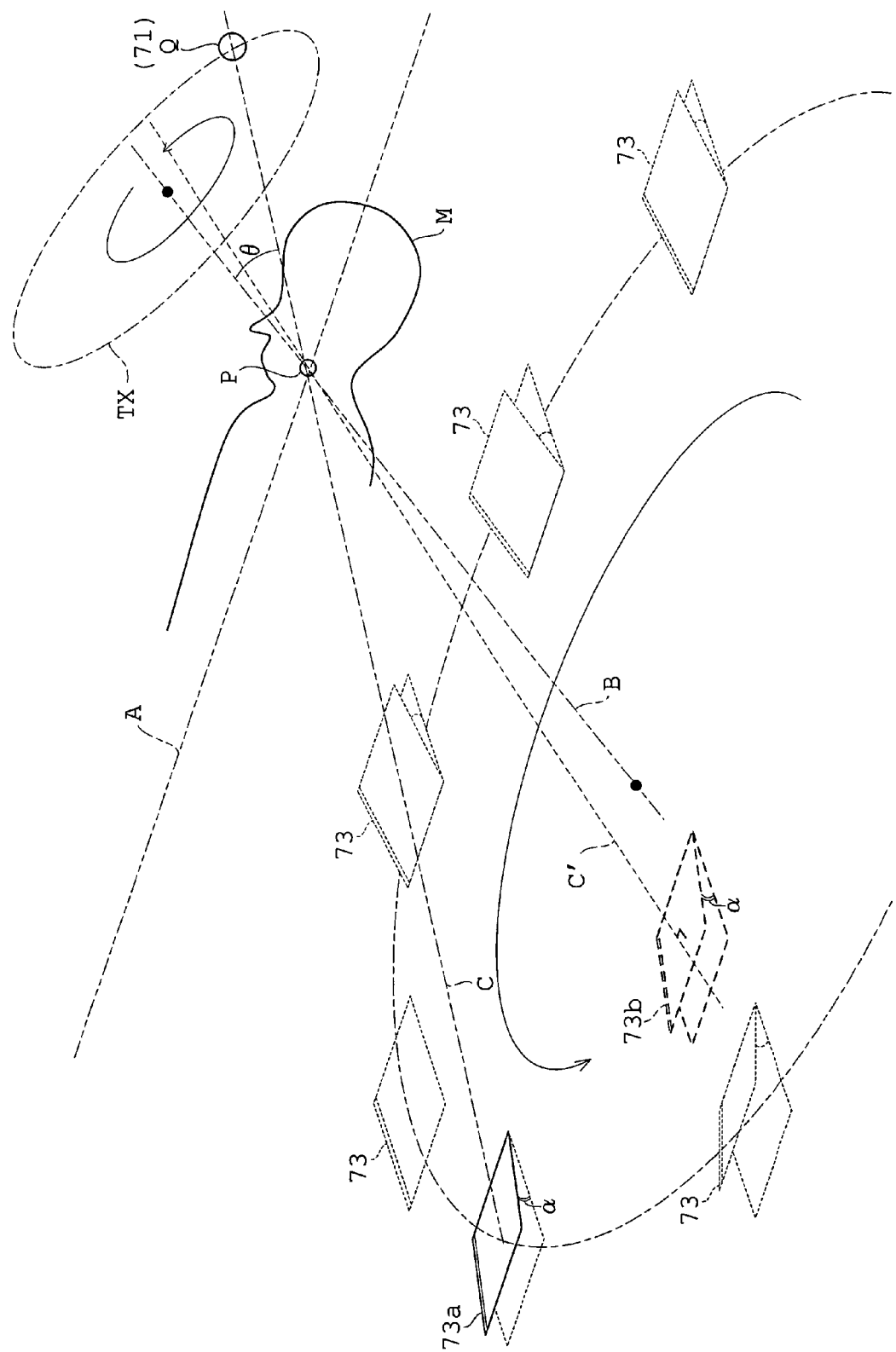
FIG. 18 is a schematic view showing a principal part of a positional relationship between rotating anode X-ray tube and FPF in time of primary scanning in a modified embodiment.

In this case, the inclination of the FPD 73, preferably, is such that the detecting plane of the FPD 73 is perpendicular to a direction corresponding to the radiation axis C from which the component along the body axis A is subtracted. This will be particularly described with reference to FIG. 18. First, the direction corresponding to the radiation axis C from which the component along the body axis A is subtracted is represented by axis C' in FIG. 18. Then, imagine an FPD 73b having a detecting plane perpendicular to the axis C'. Next, incline an FPD 73a at angle α equal to inclination angle α of the imaginary FPD 73b. The FPD 73 is thereby inclined while keeping the rows of detecting elements d (u-axis) parallel to the body axis A. This allows a braid or the like to be formed on the detecting plane conveniently.

(4) In each embodiment described hereinbefore, the FPD 6 (73) is shaped planar or curved. Such a shape is not limitative.

Figure 19:
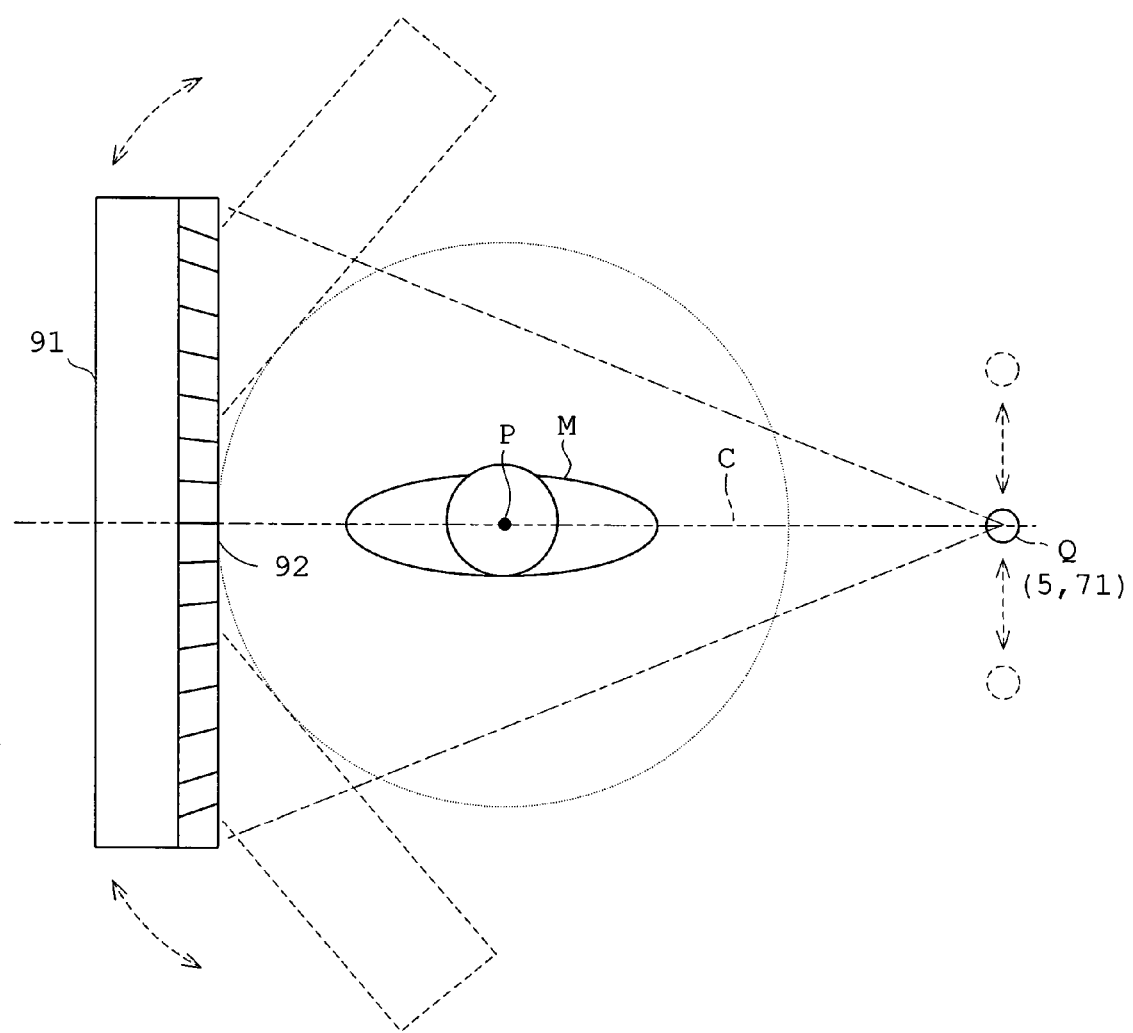
FIG. 19 is a side view of an FPD in a modified embodiment.

As shown in FIG. 19, for example, an FPD 91 having a flat detecting plane may include a braid 92 with shields arranged parallel to the body axis A.

Figure 20:
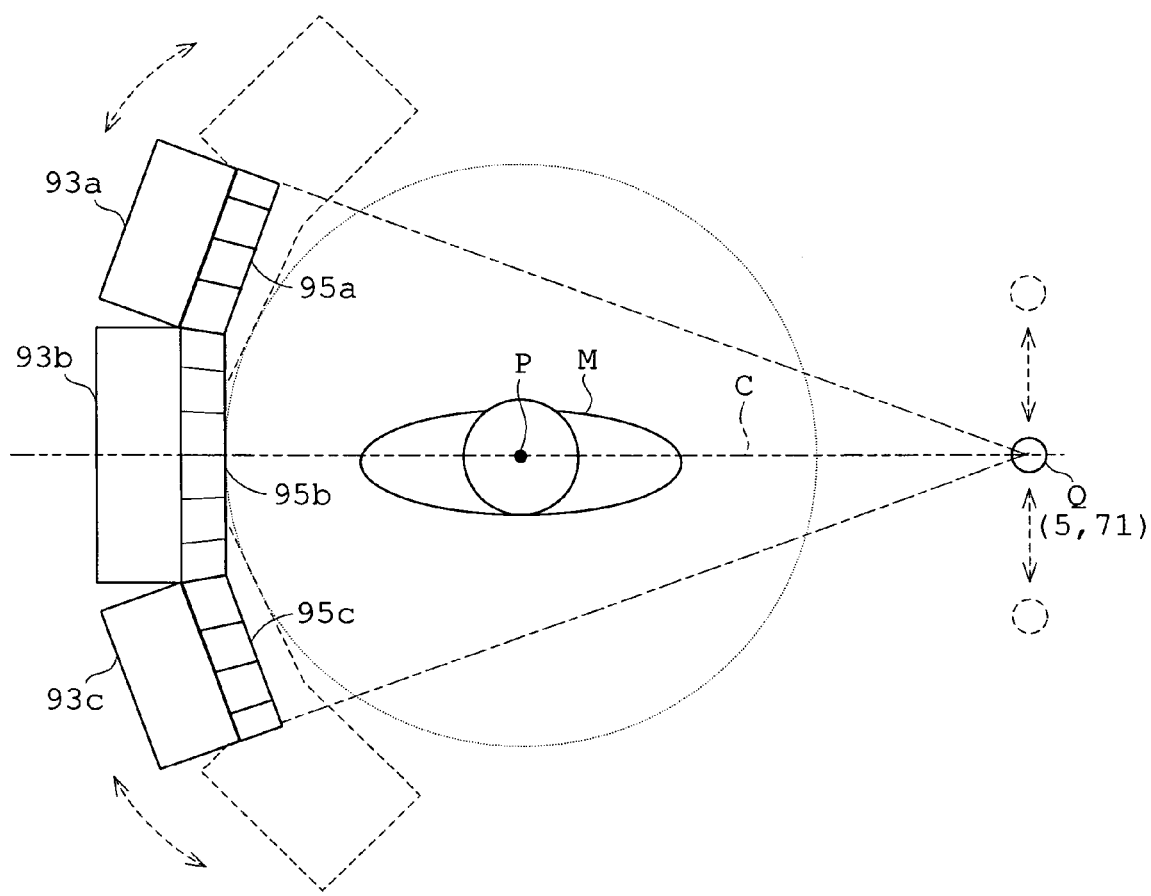
FIG. 20 is a side view of an FPD in a modified embodiment.

As shown in FIG. 20, an FPD may include three split FPDs 93a, 93b and 93c. In this case, the split FPDs 93a, 93b and 93c may have split braids 95a, 95b and 95c, respectively.

Figure 21:
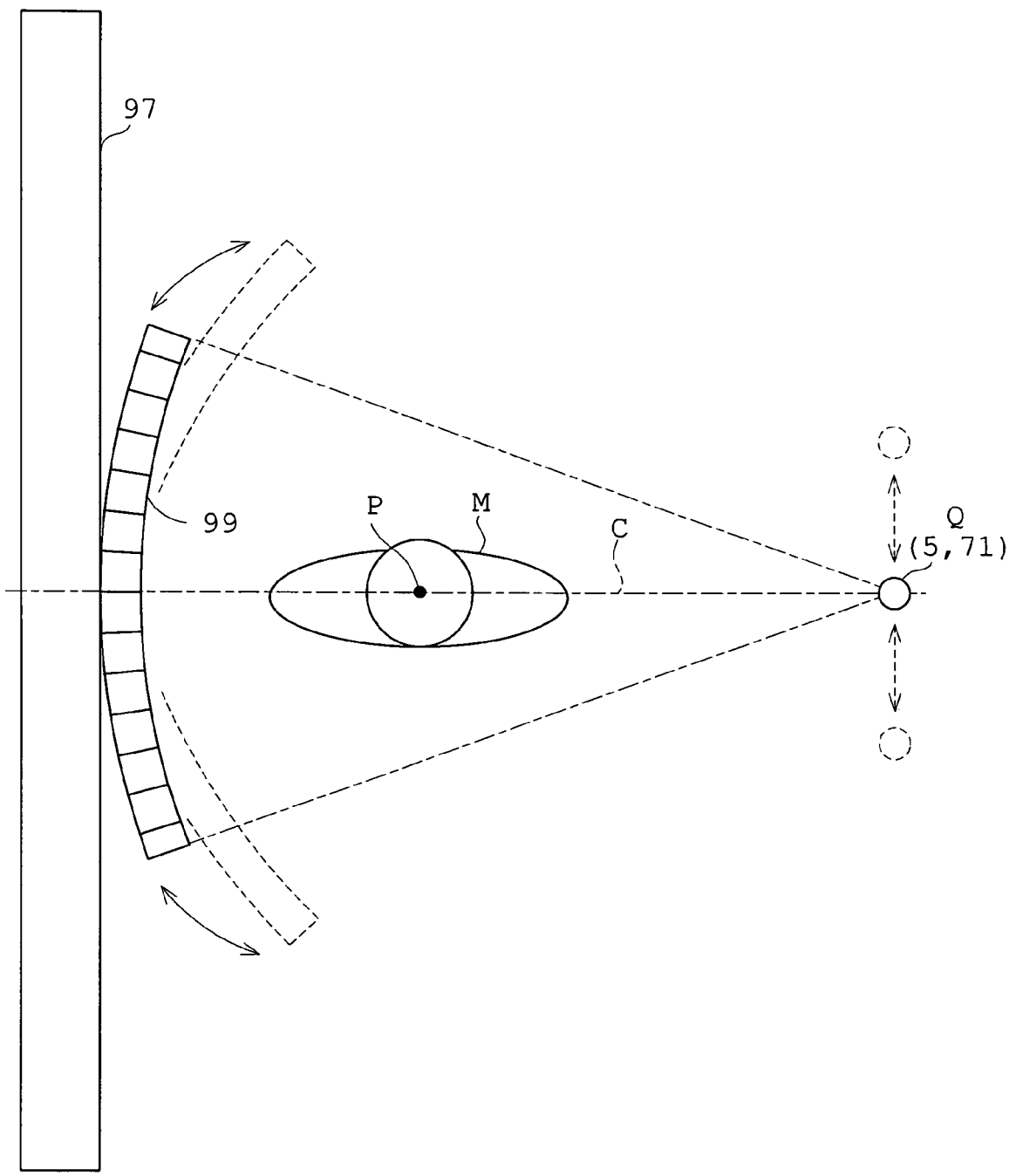
FIG. 21 is a side view of an FPD in a modified embodiment.

(5) In each embodiment described hereinbefore, the FPD 6 (73) is moved about the sectional axis B in time of the primary scanning. This is not limitative. As shown in FIG. 21, a stationary FPD 97 may have a detecting plane large enough to cover varied positions of the rotating anode X-ray tube 5 (71) movable about the sectional axis B for primary scanning. In this case, the FPD 97 is installed so that the rows or columns of detecting elements d are parallel to the body axis A. Consequently, in time of the primary scanning and secondary scanning, the rows or columns of detecting elements d are constantly maintained parallel to the body axis A.

It is also possible to form a braid 99 on the detecting plane of the FPD 97. Further, the braid 99 may be moved in a combination of a linear motion component along the body axis A and an arcuate motion component about the body axis A. In this case, a braid moving device for moving the braid 99 may use, as appropriate, the construction for moving the FPD 73 disclosed in the second embodiment. Part of the primary scanning device such as the rotary motor 31 and rotary shaft 32 may serve as the braid moving device.

(6) In the embodiments described hereinbefore, the rotating anode X-ray tube 5 (71) is movable about the sectional axis B in the primary scanning. The X-ray tube may be adapted movable in a similar way to the FPD 73 disclosed in the second embodiment.

Specifically, the rotating anode X-ray tube may be moved in a combination of a linear motion component along the body axis A and an arcuate motion component about the body axis A. For example, the X-ray tube may be moved along a curve linking intersections of a virtual cylinder Ac about the body axis A and a virtual cylinder Bc about the sectional axis B.

(7) Each foregoing embodiment has been described, taking the FPD 6 (73) for example. This invention is applicable to any X-ray detector having a plurality of detecting elements d arranged on the detecting plane.

In each embodiment described above, the FPD 6 (73) is a direct conversion type detector. This is not limitative. For example, the invention is applicable also to a detector of the indirect conversion type with a scintillator for converting incident X rays into light, and a semiconductor layer formed of a light sensitive material for converting the light to charge information.

(8) In each embodiment mentioned above, the FPD 6 (73) is a detector for detecting incident X rays. What is detected is not limited to X rays. The invention is applicable also to a detection of incident radiation, electromagnetic waves or light, other than X rays.

(9) In each embodiment described hereinbefore, the radiographic apparatus is designed for medical use. This is not limitative. The invention is applicable also to radiographic apparatus used in the industrial fields, such as for non-destructive testing, RI (Radio Isotope) inspection, and optical inspection, or in the nuclear field, for example. In each embodiment, the object under examination is described as patient M. The object under examination is of course not limited to the human body.

(10) Each embodiment has been described using the body axis A of the patient M. The invention is not limited by the term "body axis" in particular. The body axis is variable, as appropriate, to any one axis extending perpendicular to the sectional axis and passing through a site of interest of the object under examination.

This invention may be embodied in other specific forms without departing from the spirit or essential attributes thereof and, accordingly, reference should be made to the appended claims, rather than to the foregoing specification, as indicating the scope of the invention.

What is claimed is:

1. A radiographic apparatus for obtaining three-dimensional sectional images, comprising:
   a radiation source for emitting electromagnetic waves to an object under examination;
   a detecting device opposed to said radiation source across the object for obtaining projection data of the object from the electromagnetic waves transmitted through the object;
   a primary scanning device for performing a primary scanning by moving at least said radiation source to rotate a radiation axis linking said radiation source and said detecting device about a sectional axis passing through a site of interest of the object, while inclining said radiation axis at a predetermined angle to said sectional axis; and
   an image processing device for performing a reconstruction process based on a group of projection data obtained from said detecting device at each point of time in the primary scanning to acquire a three-dimensional sectional image;
   wherein said detecting device has a flat or curved detecting plane with a plurality of detecting elements arranged in rows and columns extending in two intersecting axial directions for detecting the electromagnetic waves, the rows or columns of said detecting elements being, in time of the primary scanning, constantly parallel to one axis extending perpendicular to said sectional axis and passing through said site of interest of the object.

2. An apparatus as defined in claim 1, wherein said primary scanning device is arranged to move said radiation source about the sectional axis, and move said detecting device about the sectional axis.

3. An apparatus as defined in claim 1, wherein said primary scanning device is arranged also to incline said detecting device according to a position of said detecting device, so that said detecting plane is perpendicular to a direction corresponding said radiation axis from which a component along said one axis is subtracted.

4. An apparatus as defined in claim 1, wherein said primary scanning device is arranged to move said detecting device along a curve linking intersections of a virtual cylinder about said sectional axis and a virtual cylinder about said one axis.

5. An apparatus as defined in claim 4, wherein said primary scanning device is arranged to move said radiation source along the curve linking intersections of the virtual cylinder about said sectional axis and the virtual cylinder about said one axis.

6. An apparatus as defined in claim 1, wherein movement of said detecting device by said primary scanning device is realized in a combination of a linear motion component along said one axis and a rotational motion component on an arc about said one axis.

7. An apparatus as defined in claim 6, wherein movement of said radiation source by said primary scanning device is realized in the combination of the linear motion component along said one axis and the rotational motion component on the arc about said one axis.

8. An apparatus as defined in claim 1, wherein said primary scanning device is arranged to move said detecting device along a curve linking intersections of a virtual cone formed at said predetermined angle about the sectional axis, with an intersection of said one axis and said sectional axis providing an apex, and a virtual cylinder about said one axis.

9. An apparatus as defined in claim 1, wherein said detecting plane has a braid disposed thereon for removing scattered parts of the electromagnetic waves, said primary scanning device moving said braid with said detecting device.

10. An apparatus as defined in claim 1, wherein said primary scanning device is arranged to rotate only said radiation source about the sectional axis, and said detecting device is sized to cover varied positions of said radiation source rotated by said primary scanning device, said detecting device standing still when said primary scanning device rotates said radiation source.

11. An apparatus as defined in claim 10, further comprising a braid disposed on said detecting plane for removing scattered parts of the electromagnetic waves, and a braid moving device for moving said braid in a combination of a linear motion component along said one axis and a rotational motion component on an arc about said one axis, said braid moving device maintaining said braid opposed to said radiation source.

12. An apparatus as defined in claim 1, further comprising a secondary scanning device for performing a secondary scanning by moving said radiation source and said detecting device to rotate said radiation axis about said one axis, said image processing device further performing a reconstruction process based on a group of projection data obtained from said detecting device at each point of time in the secondary scanning.

13. An apparatus as defined in claim 1, wherein said primary scanning device includes a turntable for rotating a holding rod along a circular track about the sectional axis, a support member joined to said holding rod through a bearing for supporting said detecting device, and a restricting device for restricting rotation of said support member about said bearing.

14. An apparatus as defined in claim 13, wherein said turntable is rotatable about the sectional axis, and said holding rod is disposed eccentrically of said turntable.

15. An apparatus as defined in claim 1, wherein said radiation source emits X rays, and said detecting device detects the X rays.

16. An apparatus as defined in claim 15, wherein said radiation source is a rotating anode X-ray tube, and said detecting device is a flat panel X-ray detector.

17. An apparatus as defined in claim 9, wherein said braid includes a plurality of shields parallel to the rows or columns of said detecting elements.

18. An apparatus as defined in claim 9, wherein said image processing device is arranged further to remove pattern components of said braid from the projection data obtained from said detecting device.

19. An apparatus as defined in claim 11, wherein said braid includes a plurality of shields parallel to the rows or columns of said detecting elements.

20. An apparatus as defined in claim 11, wherein said image processing device is arranged further to remove pattern components of said braid from the projection data obtained from said detecting device.

* * * * *